United States Patent
Jerosch et al.

(10) Patent No.: US 10,119,947 B2
(45) Date of Patent: Nov. 6, 2018

(54) PROTEIN-RICH MICROALGAL BIOMASS COMPOSITIONS OF OPTIMIZED SENSORY QUALITY

(71) Applicant: CORBION BIOTECH, INC.

(72) Inventors: Heike Jerosch, Estaires (FR); Amandine Druon, Lille (FR); Marilyne Guillemant, Aire sur la Lys (FR); Samuel Patinier, Quesnoy-sur-Deule (FR)

(73) Assignee: CORBION BIOTECH, INC., South San Francisco ( * ) Notice: Subject to any disclaimer, the term of this patent is extended or adjusted under 35 U.S.C. 154(b) by 185 days.

(21) Appl. No.: 14/910,918

(22) PCT Filed: Aug. 6, 2014

(86) PCT No.: PCT/FR2014/052046
§ 371 (c)(1),
(2) Date: Feb. 8, 2016

(87) PCT Pub. No.: WO2015/019023
PCT Pub. Date: Feb. 12, 2015

(65) Prior Publication Data
US 2016/0195503 A1 Jul. 7, 2016

(30) Foreign Application Priority Data
Aug. 7, 2013 (FR) ..................... 13 57843

(51) Int. Cl.
*G01N 33/00* (2006.01)
*G01N 30/72* (2006.01)
*C12N 1/12* (2006.01)

(52) U.S. Cl.
CPC ..... *G01N 33/0001* (2013.01); *G01N 30/7206* (2013.01); *A23V 2002/00* (2013.01); *C12N 1/12* (2013.01)

(58) Field of Classification Search
CPC .. G01N 33/0001; G01N 30/7206; C12N 1/12; A23V 2002/00
See application file for complete search history.

(56) References Cited

U.S. PATENT DOCUMENTS 2,506,540 A 5/1950 Collis
2,967,700 A 1/1961 Lee et al.
(Continued)

FOREIGN PATENT DOCUMENTS

CN 1766082 A 5/2006
CN 1837352 A 9/2006
(Continued)

OTHER PUBLICATIONS

Becker, E.W., "Micro-algae as a source of protein," *Biotechnology Advances*, Jan. 26, 2007, vol. 25, No. 2, pp. 207-210.
(Continued)

*Primary Examiner* — Jeremy C Flinders
(74) *Attorney, Agent, or Firm* — Weaver Austin Villeneuve & Sampson, LLP

(57) ABSTRACT

The invention relates to a method for determining the organoleptic quality of a protein-rich microalgal biomass composition, comprising the determination of the content of 11 volatile organic compounds, wherein the 11 volatile organic compounds are pentanal, hexanal, 1-octen-3-ol, 2-pentylfuran, octanal, 3,5-octadien-2-ol (or 3-octen-2-one), 3,5-octadien-2-one, nonanal, 2-no-nenal, (E,E)-2,4-nonadienal and hexanoic acid.

13 Claims, 5 Drawing Sheets

(56) References Cited

U.S. PATENT DOCUMENTS

| | | |
|---|---|---|
| 3,142,135 A | 7/1964 | Kathrein |
| 3,280,502 A | 10/1966 | Farrow et al. |
| 3,320,693 A | 5/1967 | Shirota et al. |
| 3,957,578 A | 5/1976 | Narita et al. |
| 3,962,466 A | 6/1976 | Nakabayashi |
| 3,983,008 A | 9/1976 | Shinozaki et al. |
| 4,005,062 A | 1/1977 | Schnell |
| 4,103,039 A | 7/1978 | Mandai et al. |
| 4,104,460 A | 8/1978 | Hasebe |
| 4,140,805 A | 2/1979 | Edwards et al. |
| 4,182,777 A | 1/1980 | Saunders et al. |
| 4,273,790 A | 6/1981 | Bosco et al. |
| 4,324,067 A | 4/1982 | Kessler |
| 4,341,038 A | 7/1982 | Bloch et al. |
| 4,373,434 A | 2/1983 | Alexander et al. |
| 4,390,561 A | 6/1983 | Blair et al. |
| 4,519,845 A | 5/1985 | Ou |
| 4,564,526 A | 1/1986 | Takashima |
| 4,627,192 A | 12/1986 | Fick |
| 4,673,490 A | 6/1987 | Subramanian et al. |
| 4,744,996 A | 5/1988 | Rakow et al. |
| 4,756,319 A | 7/1988 | Takanashi |
| 4,901,635 A | 2/1990 | Williams |
| 4,915,961 A | 4/1990 | Tanaka |
| 5,001,059 A | 3/1991 | Skatrud et al. |
| 5,130,242 A | 7/1992 | Barclay |
| 5,212,087 A | 5/1993 | Fournier et al. |
| 5,236,721 A | 8/1993 | Yung Chu et al. |
| 5,252,198 A | 10/1993 | Harrison et al. |
| 5,270,177 A | 12/1993 | Ramos Lazcano et al. |
| 5,330,913 A | 7/1994 | Nakayama |
| 5,338,673 A | 8/1994 | Thepenier et al. |
| 5,354,878 A | 10/1994 | Connemann et al. |
| 5,436,394 A | 7/1995 | Willmitzer et al. |
| 5,487,916 A | 1/1996 | Christensen |
| 5,492,938 A | 2/1996 | Kyle et al. |
| 5,518,918 A | 5/1996 | Barclay et al. |
| 5,547,699 A | 8/1996 | Iizuka et al. |
| 5,567,732 A | 10/1996 | Kyle et al. |
| 5,595,965 A | 1/1997 | Wiggins |
| 5,643,585 A | 7/1997 | Arad et al. |
| 5,656,310 A | 8/1997 | Santillo, Jr. |
| 5,680,812 A | 10/1997 | Linsgeseder |
| 5,685,218 A | 11/1997 | Kemper |
| 5,693,357 A | 12/1997 | Wong |
| 5,711,983 A | 1/1998 | Kyle et al. |
| 5,756,135 A | 5/1998 | Seeley |
| 5,792,631 A | 8/1998 | Running |
| 5,826,500 A | 10/1998 | Kemper |
| 5,888,947 A | 3/1999 | Lambert et al. |
| 5,900,370 A | 5/1999 | Running |
| 5,945,585 A | 8/1999 | Hitz et al. |
| 5,968,791 A | 10/1999 | Davis et al. |
| 6,139,897 A | 10/2000 | Goto et al. |
| 6,166,231 A | 12/2000 | Hoeksema |
| 6,255,505 B1 | 7/2001 | Bijl et al. |
| 6,294,207 B1 | 9/2001 | Christian sen et al. |
| 6,338,866 B1 | 1/2002 | Criggall et al. |
| 6,344,231 B1 | 2/2002 | Nakajo et al. |
| 6,372,460 B1 | 4/2002 | Gladue et al. |
| 6,441,208 B2 | 8/2002 | Bijl et al. |
| 6,620,427 B2 | 9/2003 | Lasekan et al. |
| 6,727,373 B2 | 4/2004 | Bijl et al. |
| 6,750,048 B2 | 6/2004 | Ruecker et al. |
| 6,867,308 B2 | 3/2005 | Bartok et al. |
| 7,053,267 B2 | 5/2006 | Knauf et al. |
| 7,063,957 B2 | 6/2006 | Chen |
| 7,214,297 B2 | 5/2007 | Wang et al. |
| 7,351,558 B2 | 4/2008 | Ruecker et al. |
| 7,468,267 B2 | 12/2008 | Monod et al. |
| 7,504,259 B2 | 3/2009 | Yadav et al. |
| 7,588,931 B2 | 9/2009 | Damude et al. |
| 7,662,598 B2 | 2/2010 | Ruecker et al. |
| 7,678,931 B2 | 3/2010 | Fichtali et al. |
| 7,781,193 B2 | 8/2010 | Ruecker et al. |
| 7,879,591 B2 | 2/2011 | Damude et al. |
| 7,883,882 B2 | 2/2011 | Franklin et al. |
| 7,914,832 B2 | 3/2011 | Uchino |
| 7,935,515 B2 | 5/2011 | Franklin et al. |
| 7,939,710 B1 | 5/2011 | Apt et al. |
| 8,029,579 B2 | 10/2011 | Knuth et al. |
| 8,043,496 B1 | 10/2011 | Schuh et al. |
| 8,119,583 B2 | 2/2012 | Day et al. |
| 8,187,860 B2 | 5/2012 | Franklin et al. |
| 8,222,010 B2 | 7/2012 | Franklin et al. |
| 8,268,610 B2 | 9/2012 | Franklin et al. |
| 8,278,261 B2 | 10/2012 | Day et al. |
| 8,283,483 B2 | 10/2012 | Williams et al. |
| 8,435,767 B2 | 5/2013 | Franklin et al. |
| 8,450,083 B2 | 5/2013 | Day et al. |
| 8,476,059 B2 | 7/2013 | Trimbur et al. |
| 8,497,116 B2 | 7/2013 | Trimbur et al. |
| 8,512,999 B2 | 8/2013 | Trimbur et al. |
| 8,518,689 B2 | 8/2013 | Trimbur et al. |
| 8,530,207 B2 | 9/2013 | Watts et al. |
| 8,592,188 B2 | 11/2013 | Franklin et al. |
| 8,633,012 B2 | 1/2014 | Franklin et al. |
| 8,647,397 B2 | 2/2014 | Trimbur et al. |
| 8,674,180 B2 | 3/2014 | Franklin et al. |
| 8,697,402 B2 | 4/2014 | Trimbur et al. |
| 8,697,427 B2 | 4/2014 | Franklin et al. |
| 8,747,834 B2 | 6/2014 | Brinkmann et al. |
| 8,765,424 B2 | 7/2014 | Franklin et al. |
| 8,772,575 B2 | 7/2014 | Franklin et al. |
| 8,790,914 B2 | 7/2014 | Trimbur et al. |
| 8,802,422 B2 | 8/2014 | Trimbur et al. |
| 8,822,176 B2 | 9/2014 | Day et al. |
| 8,822,177 B2 | 9/2014 | Day et al. |
| 8,846,352 B2 | 9/2014 | Chua et al. |
| 8,846,375 B2 | 9/2014 | Franklin et al. |
| 8,852,885 B2 | 10/2014 | Franklin et al. |
| 8,889,401 B2 | 11/2014 | Trimbur et al. |
| 8,889,402 B2 | 11/2014 | Trimbur et al. |
| 8,945,908 B2 | 2/2015 | Franklin et al. |
| 8,951,777 B2 | 2/2015 | Franklin et al. |
| 9,062,294 B2 | 6/2015 | Franklin et al. |
| 9,066,527 B2 | 6/2015 | Franklin et al. |
| 9,068,213 B2 | 6/2015 | Franklin et al. |
| 9,102,973 B2 | 8/2015 | Franklin et al. |
| 9,109,239 B2 | 8/2015 | Franklin et al. |
| 9,345,730 B2 | 5/2016 | Brinkmann et al. |
| 2002/0122868 A1 | 9/2002 | Floeter et al. |
| 2003/0097686 A1 | 5/2003 | Knauf et al. |
| 2003/0138477 A1 | 7/2003 | Barclay |
| 2003/0229237 A1 | 12/2003 | Haas et al. |
| 2004/0162266 A1 | 8/2004 | Myatt et al. |
| 2004/0230085 A1 | 11/2004 | Jakkula et al. |
| 2005/0005333 A1 | 1/2005 | Ruezinsky et al. |
| 2005/0008656 A1 | 1/2005 | Meredith et al. |
| 2005/0153002 A1 | 7/2005 | Socla Rosales et al. |
| 2005/0170479 A1 | 8/2005 | Weaver et al. |
| 2005/0262588 A1 | 11/2005 | Dehesh et al. |
| 2005/0266537 A1 | 12/2005 | Chen |
| 2006/0094088 A1 | 5/2006 | Picataggio et al. |
| 2006/0094089 A1 | 5/2006 | Barclay |
| 2006/0122410 A1 | 6/2006 | Fichtali et al. |
| 2006/0286205 A1 | 12/2006 | Fichtali et al. |
| 2007/0009988 A1 | 1/2007 | Monod et al. |
| 2007/0099280 A1 | 5/2007 | Barclay |
| 2007/0118916 A1 | 5/2007 | Puzio et al. |
| 2007/0160728 A1 | 7/2007 | Rudie et al. |
| 2007/0166266 A1 | 7/2007 | Dillon et al. |
| 2007/0167396 A1 | 7/2007 | Dillon et al. |
| 2007/0218183 A1 | 9/2007 | Nakhasi et al. |
| 2007/0261138 A1 | 11/2007 | Graham et al. |
| 2008/0019997 A1 | 1/2008 | Shaish et al. |
| 2008/0107776 A1 | 5/2008 | Prakash et al. |
| 2008/0160593 A1 | 7/2008 | Oyler |
| 2008/0206379 A1 | 8/2008 | Fabritius et al. |
| 2008/0283803 A1 | 11/2008 | Rapp et al. |
| 2009/0004715 A1 | 1/2009 | Trimbur et al. |
| 2009/0011480 A1 | 1/2009 | Trimbur et al. |
| 2009/0035842 A1 | 2/2009 | Trimbur et al. |
| 2009/0047721 A1 | 2/2009 | Trimbur et al. |

(56) References Cited

U.S. PATENT DOCUMENTS

| | | |
|---|---|---|
| 2009/0061493 A1 | 3/2009 | Trimbur et al. |
| 2009/0064567 A1 | 3/2009 | Lippmeier et al. |
| 2009/0068315 A1 | 3/2009 | Hundscheid et al. |
| 2009/0099260 A1 | 4/2009 | Namal Senanayake et al. |
| 2009/0142322 A1 | 6/2009 | Ye |
| 2009/0148918 A1 | 6/2009 | Trimbur et al. |
| 2009/0211150 A1 | 8/2009 | Wu et al. |
| 2009/0234146 A1 | 9/2009 | Cooney et al. |
| 2009/0274736 A1 | 11/2009 | Dillon et al. |
| 2009/0298159 A1 | 12/2009 | Wu et al. |
| 2010/0010088 A1 | 1/2010 | Chilton et al. |
| 2010/0021912 A1 | 1/2010 | Farese et al. |
| 2010/0028488 A1 | 2/2010 | Lo et al. |
| 2010/0058651 A1 | 3/2010 | Knuth et al. |
| 2010/0120643 A1 | 5/2010 | Brown et al. |
| 2010/0151112 A1 | 6/2010 | Franklin et al. |
| 2010/0151538 A1 | 6/2010 | Franklin et al. |
| 2010/0151567 A1 | 6/2010 | Franklin et al. |
| 2010/0170144 A1 | 7/2010 | Day et al. |
| 2010/0186117 A1 | 7/2010 | Fabijanski et al. |
| 2010/0196575 A1 | 8/2010 | Sanchez et al. |
| 2010/0239712 A1 | 9/2010 | Brooks et al. |
| 2010/0297292 A1 | 11/2010 | Brooks et al. |
| 2010/0297295 A1 | 11/2010 | Brooks et al. |
| 2010/0297296 A1 | 11/2010 | Brooks et al. |
| 2010/0297323 A1 | 11/2010 | Brooks et al. |
| 2010/0297325 A1 | 11/2010 | Brooks et al. |
| 2010/0297331 A1 | 11/2010 | Brooks et al. |
| 2010/0303957 A1 | 12/2010 | Brooks et al. |
| 2010/0303961 A1 | 12/2010 | Brooks et al. |
| 2010/0303989 A1 | 12/2010 | Brooks et al. |
| 2010/0303990 A1 | 12/2010 | Brooks et al. |
| 2010/0323413 A1 | 12/2010 | Trimbur et al. |
| 2010/0323414 A1 | 12/2010 | Trimbur et al. |
| 2011/0014665 A1 | 1/2011 | Trimbur et al. |
| 2011/0015417 A1 | 1/2011 | Trimbur et al. |
| 2011/0044915 A1 | 2/2011 | Ribadeau-Dumas |
| 2011/0047863 A1 | 3/2011 | Trimbur et al. |
| 2011/0072714 A1 | 3/2011 | Gaertner et al. |
| 2011/0190522 A1 | 8/2011 | Trimbur et al. |
| 2011/0203168 A1 | 8/2011 | Franklin et al. |
| 2011/0252696 A1 | 10/2011 | Franklin et al. |
| 2011/0256268 A1 | 10/2011 | Franklin et al. |
| 2011/0256282 A1 | 10/2011 | Piechocki et al. |
| 2011/0293785 A1 | 12/2011 | Franklin et al. |
| 2011/0294174 A1 | 12/2011 | Franklin et al. |
| 2011/0305740 A1 | 12/2011 | Boursier |
| 2012/0027724 A1 | 2/2012 | Brinkmann et al. |
| 2012/0028319 A1 | 2/2012 | Trimbur et al. |
| 2012/0034662 A1 | 2/2012 | Hu et al. |
| 2012/0122192 A1 | 5/2012 | Trimbur et al. |
| 2012/0128851 A1 | 5/2012 | Brooks et al. |
| 2012/0149075 A1 | 6/2012 | Day et al. |
| 2012/0164701 A1 | 6/2012 | Trimbur et al. |
| 2012/0203018 A1 | 8/2012 | Franklin et al. |
| 2012/0269949 A1 | 10/2012 | Nakajima et al. |
| 2012/0277452 A1 | 11/2012 | Franklin et al. |
| 2012/0277453 A1 | 11/2012 | Franklin et al. |
| 2012/0283460 A1 | 11/2012 | Franklin et al. |
| 2012/0288930 A1 | 11/2012 | Trimbur et al. |
| 2012/0324784 A1 | 12/2012 | Franklin et al. |
| 2012/0329109 A1 | 12/2012 | Chua et al. |
| 2013/0004646 A1 | 1/2013 | Franklin et al. |
| 2013/0005005 A1 | 1/2013 | Day et al. |
| 2013/0006006 A1 | 1/2013 | Day et al. |
| 2013/0031678 A1 | 1/2013 | Zheng et al. |
| 2013/0034887 A1 | 2/2013 | Franklin et al. |
| 2013/0078709 A1 | 3/2013 | Franklin et al. |
| 2013/0089916 A1 | 4/2013 | Franklin et al. |
| 2013/0096211 A1 | 4/2013 | Franklin et al. |
| 2013/0102039 A1 | 4/2013 | Franklin et al. |
| 2013/0122180 A1 | 5/2013 | Brooks et al. |
| 2013/0165677 A1 | 6/2013 | Franklin et al. |
| 2013/0197247 A1 | 8/2013 | Franklin et al. |
| 2013/0273621 A1 | 10/2013 | Franklin et al. |
| 2013/0295268 A1 | 11/2013 | Day et al. |
| 2013/0296591 A1 | 11/2013 | Day et al. |
| 2013/0309358 A1 | 11/2013 | Norris |
| 2013/0323382 A1 | 12/2013 | Franklin et al. |
| 2013/0330790 A1 | 12/2013 | Trimbur et al. |
| 2013/0338385 A1 | 12/2013 | Franklin et al. |
| 2014/0106051 A1 | 4/2014 | Lefevre et al. |
| 2014/0170716 A1 | 6/2014 | Trimbur et al. |
| 2014/0212570 A1 | 7/2014 | Norris et al. |
| 2014/0234479 A1 | 8/2014 | Norris et al. |
| 2014/0249342 A1 | 9/2014 | Franklin et al. |
| 2014/0256024 A1 | 9/2014 | Franklin et al. |
| 2014/0256600 A1 | 9/2014 | Dillon et al. |
| 2014/0287114 A1 | 9/2014 | Finely et al. |
| 2014/0305031 A1 | 10/2014 | Day et al. |
| 2014/0315267 A1 | 10/2014 | Franklin et al. |
| 2014/0328906 A1 | 11/2014 | Brinkmann et al. |
| 2014/0336100 A1 | 11/2014 | Day et al. |
| 2014/0357746 A1 | 12/2014 | Ngantung et al. |
| 2014/0377847 A1 | 12/2014 | Franklin et al. |
| 2015/0073163 A1 | 3/2015 | Chua et al. |
| 2015/0125914 A1 | 5/2015 | Franklin et al. |
| 2015/0218604 A1 | 8/2015 | Franklin et al. |
| 2015/0275149 A1 | 10/2015 | Dummer et al. |
| 2015/0344917 A1 | 12/2015 | Franklin et al. |
| 2015/0374012 A1 | 12/2015 | Klamczynska et al. |
| 2016/0021923 A1 | 1/2016 | Paulsen et al. |
| 2016/0143336 A1 | 5/2016 | Druon et al. |
| 2016/0161460 A1 | 6/2016 | Druon et al. |
| 2016/0192691 A1 | 7/2016 | Druon et al. |
| 2016/0324167 A1 | 11/2016 | Brooks et al. |
| 2017/0119005 A1 | 5/2017 | Piechocki et al. |
| 2018/0092389 A1 | 4/2018 | Norris |

FOREIGN PATENT DOCUMENTS

| | | |
|---|---|---|
| CN | 1940021 A | 4/2007 |
| CN | 101037639 | 9/2007 |
| CN | 101130513 A | 2/2008 |
| DE | 10 2006 056454 A1 | 5/2008 |
| EP | 0528466 A1 | 7/1992 |
| EP | 0562504 B1 | 11/1995 |
| EP | 1178118 | 2/2002 |
| EP | 1681337 | 7/2006 |
| EP | 1741767 | 1/2007 |
| FR | 2 924 126 A1 | 5/2009 |
| GB | 824151 | 11/1959 |
| JP | 45-17146 | 6/1970 |
| JP | S57-0150379 A | 9/1982 |
| JP | 58-184264 | 10/1983 |
| JP | S60-75244 A | 4/1985 |
| JP | 62-061568 | 3/1987 |
| JP | 04-108374 | 4/1992 |
| JP | 04-077189 | 10/1993 |
| JP | 05-276963 | 10/1993 |
| JP | 06-253872 A | 9/1994 |
| JP | 07-008217 A | 1/1995 |
| JP | 07-075557 | 3/1995 |
| JP | 09-012466 | 1/1997 |
| JP | 09-252707 | 9/1997 |
| JP | 409252707 A | 9/1997 |
| JP | 2000-175680 | 6/2000 |
| JP | 2000-175696 | 6/2000 |
| JP | 2001-095481 | 4/2001 |
| JP | 2001-292751 A | 10/2001 |
| JP | 2002-125601 A | 5/2002 |
| JP | 2003023966 A | 1/2003 |
| JP | 2004-049079 A | 2/2004 |
| JP | 2004-275173 A | 10/2004 |
| JP | 2006-014700 A | 1/2006 |
| JP | 2008-148663 | 7/2008 |
| JP | 2008-253146 | 10/2008 |
| JP | 2016-198117 | 12/2016 |
| WO | WO 91/018105 | 11/1991 |
| WO | WO 94/010288 A2 | 5/1994 |
| WO | WO 97/040698 A1 | 11/1997 |
| WO | WO 99/037166 A1 | 7/1999 |
| WO | WO 00/011682 A1 | 3/2000 |
| WO | WO 00/61740 A1 | 10/2000 |

(56) References Cited

FOREIGN PATENT DOCUMENTS

| | | |
|---|---|---|
| WO | WO 00/066750 A2 | 11/2000 |
| WO | WO 02/008403 | 1/2002 |
| WO | WO 06/122299 A2 | 11/2006 |
| WO | WO 07/027669 | 3/2007 |
| WO | WO 07/094498 | 8/2007 |
| WO | WO 07/121100 | 10/2007 |
| WO | WO 07/134294 A2 | 11/2007 |
| WO | WO 08/002643 A2 | 1/2008 |
| WO | WO 08/060571 | 5/2008 |
| WO | WO 08/083352 A1 | 7/2008 |
| WO | WO 08/130372 A2 | 10/2008 |
| WO | WO 08/134836 A2 | 11/2008 |
| WO | WO 09/076559 | 6/2009 |
| WO | WO 09/105620 A1 | 8/2009 |
| WO | WO 09/126843 A2 | 10/2009 |
| WO | WO 09/147340 A1 | 12/2009 |
| WO | WO 10/007331 A2 | 1/2010 |
| WO | WO 10/007332 A3 | 1/2010 |
| WO | WO 10/019813 | 2/2010 |
| WO | WO 10/063031 A2 | 6/2010 |
| WO | WO 10/063032 A2 | 6/2010 |
| WO | WO 10/111698 | 9/2010 |
| WO | WO 10/120939 | 10/2010 |
| WO | WO 11/026008 | 3/2011 |
| WO | WO 11/090730 A1 | 7/2011 |
| WO | WO 11/130573 A1 | 10/2011 |
| WO | WO 11/130576 A1 | 10/2011 |
| WO | WO 11/130578 A2 | 10/2011 |
| WO | WO 11/150410 A2 | 12/2011 |
| WO | WO 11/150411 A1 | 12/2011 |
| WO | WO 12/061647 | 5/2012 |
| WO | WO 12/106560 A1 | 8/2012 |
| WO | WO 12/154626 A1 | 11/2012 |
| WO | WO 2013/059023 A1 | 4/2013 |
| WO | WO 13/082186 A2 | 6/2013 |
| WO | WO 13/158938 | 10/2013 |
| WO | WO 14/176515 A2 | 10/2014 |
| WO | WO 15/051319 A2 | 4/2015 |

OTHER PUBLICATIONS

Fradique, M., etal., "Incorporation of *Chlorella vulgaris* and *Spirulina maxima* biomass in pasta products. Part 1: Preparation and evaluation," *Journal of the Science of Food and Agriculture*, Aug. 15, 2010, vol. 90, No. 10, pp. 1656-1664.

Santos, J.E.R., et al., "Analysis of Volatile Organic Compounds in Virgin Coconut Oil and their Sensory Attibutes," *Philippine Journal of Science*, Dec. 19, 2011, vol. 140, No. 2, pp. 161-171.

Satchwill, T., "Drinking Water Taste and Odor: Compound Identification and Treatment," Thesis, University of Calgary, Alberta, Canada, Apr. 1, 2001, pp. 1-171, retrieved from internet: http://www.collectionscanada.gc.ca/obj/s4/f2/dsk3/ftp05/MQ6477.pdf.

Stone, H., et al., "Sensory Evaluation by Quantitative Descriptive Analysis," *Food Technology*, Nov. 1974, pp. 24-34.

Sun, S.-M., et al., "Volatile compounds of the green alga, *Capsosiphon fulvescens*," *Journal of Applied Phycology*, Sep. 27, 2012, vol. 24, No. 5, pp. 1003-1013.

Written Opinion in International Application No. PCT/FR2014/052046, dated Sep. 19, 2014, pp. 1-11.

U.S. Appl. No. 13/837,514, Non-Final Office Action, dated May 20, 2014.

U.S. Appl. No. 14/166,382, Non-Final Office Action, dated Jan. 15, 2015.

U.S. Appl. No. 13/837,514, Final Office Action, dated Jan. 28, 2015.

U.S. Appl. No. 14/166,382, Notice of Allowance, dated Oct. 23, 2015.

U.S. Appl. No. 13/837,514, Non-Final Office Action, dated Aug. 5, 2016.

U.S. Appl. No. 14/166,382, Non-Final Office Action, dated Aug. 10, 2016.

U.S. Appl. No. 14/166,382, Non-Final Office Action, dated Jun. 15, 2017.

U.S. Appl. No. 13/837,514, Non-Final Office Action, dated Aug. 10, 2017.

U.S. Appl. No. 14/900,654, Restriction Requirement, dated Jul. 7, 2017.

U.S. Appl. No. 14/900,654, Non-Final Office Action, dated Sep. 20, 2017.

International Search Report, dated May 12, 2014, for International Patent Application No. PCT/US2014/13405.

Written Opinion of the International Searching Authority, dated May 12, 2014, for International Patent Application No. PCT/US2014/13405.

International Preliminary Examination Report, dated Jul. 28, 2015, for International Patent Application No. PCT/US2014/13405.

European Search Report and European Search Opinion for application EP14742729.8 dated Sep. 20, 2016.

Australian Patent Application No. 2014209015, Examination Report No. 1, dated Dec. 7, 2016.

Australian Patent Application No. 2014209015, Examination Report No. 2, dated Aug. 10, 2017.

Australian Patent Application No. 2014209015, Examination Report No. 3, dated Dec. 4, 2017.

Official Action, dated Dec. 28, 2017 for Japanese Patent Application No. 2015-555414.

Memorandum Order, *Roquette Frères, S.A. v. Solazyme, Inc.*, C.A. No. 14-1442-SLR, District Court for the District of Delaware, Jan. 12, 2016.

Plaintiff and Counter-Defendant Roquette Frères, S.A.'s Reply Brief in Support of Its Motion for Stay Pending Appeal, *Roquette Frères, S.A. v. Solazyme, Inc.*, C.A. No. 14/1442-SLR, District Court for the District of Delaware, Jan. 8, 2016.

Defendant and Counterclaimant Solazyme, Inc.'s Brief in Opposition to Plaintiff and Counter-Defendant Roquette Freres, S.A.'S Motion to Stay Pending Appeal, *Roquette Frères, S.A. v. Solazyme, Inc.*, C.A. No. 14/1442-SLR, District Court for the District of Delaware, Jan. 6, 2016.

Declaration of Jonathan Wolfson in Support of Defendant and Counterclaimant Solazyme, Inc.'s Opposition to Plaintiff and Counterclaimant Roquette Freres, S.A.'s Motion to Stay Pending Appeal, *Roquette Freres, S.A. v. Solazyme, Inc.*, C.A. No. 14-1442-SLR, District Court for the District of Delaware, Jan. 6, 2016, Redacted Public Version.

Declaration of Jeffrey M. Goehring in Support of Plaintiff and Counter-Defendant Roquette Frères, S.A.'S Brief Motion for Stay Pending Appeal, *Roquette Frères, S.A. v. Solazyme, Inc.*, C.A. No. 14/1442-SLR, District Court for the District of Delaware, Dec. 28, 2015, Redacted Version • Exhibit 1, BASF and Solazyme Launch the First Commercial Microalgae-Derived Betaine Surfactant, Solazyme, Inc., Jul. 28, 2015 • Exhibit 2, Solazyme Bunge Renewable Oils Completes Key Redundant Power and Steam Supplies, Solazyme Bunge Renewable Oils, Jun. 30, 2015 • Exhibit 3, Solazyme Receives FDA GRAS No Questions Letter for High Oleic Algae Oil, Solazyme, Inc., Feb. 24, 2015 • Exhibit 4, Solazyme's (SZYM) CEO Jonathan Wolfson on Q1 2015 Results—Earnings Call Transcript, Solazyme, Inc., May 6, 2015 • Exhibit 5, Solazyme's (SZYM) CEO Jonathan Wolfson on Q2 2015 Results—Earnings Call Transcript, Solazyme, Inc., Jul. 30, 2015 • Exhibit 6, Solazyme's (SZYM) CEO Jonathan Wolfson on Q4 2014 Results—Earnings Call Transcript, Solazyme, Feb. 26, 2015 • Exhibit 7, Redacted in Its Entirety.

Motion to Stay Pending Appeal and Order Granting Motion to Stay Pending Appeal, *Roquette Frères, S.A. v. Solazyme, Inc.*, C.A. No. 14-1442-SLR, District Court for the District of Delaware, Dec. 28, 2015.

Memorandum of Law in Support of Motion by Roquette Frères, S.A. For a Stay Pending Appeal, *Roquette Frères, S.A. v. Solazyme, Inc.*, C.A. No. 14-1442-SLR, District Court for the District of Delaware, Dec. 28, 2015.

Email dated Nov. 3, 2015, from Gerald Suh of Solazyme, Inc., to Jeffrey M. Goehring of Young & Thompson International Patent & Trademark Law (counsel for Roquette Frères, S.A.).

(56) References Cited

OTHER PUBLICATIONS

Letter dated Oct. 6, 2015, from Jeffrey M. Goehring of Young & Thompson International Patent & Trademark Law (counsel for Roquette Frères, S.A.) to Gerald Suh of Solazyme, Inc., and R. James Balls and William E. McShane of Novak Druce Connolly Bove + Quigg LLP (counsel for Solazyme Roquette Nutritionals, LLC), which included the following enclosures: Exhibits 1, 9-12, and 14-15 to the Declaration of Jeffrey M. Goehring in Support of Roquette Frères, S.A.'s Brief in Support of its Motion for Summary Judgment of Solazyme, Inc.'s Claim for Misappropriation of Trade Secrets, *Roquette Frères, S.A.* v. *Solazyme, Inc.*, C.A. No. 14-01442, District Court for the District of Delaware, D.I. 141, Jun. 22, 2015, Redacted Version; Exibits 2-8 to the Declaration for Jeffrey M. Goehring in Support of Roquette Frères, S.A.'s Brief in Support of its Motion for Summary Judgment of Solazyme, Inc.'s Claim for Misappropriation of Trade Secrets, *Roquette Frères, S.A.* v. *Solazyme, Inc.*, C.A. No. 14/01442, District Court for the District of Delaware, D.I. 112-1, Jun. 22, 2015; Exhibit 13 to the Declaration of Jeffrey M. Goehring in Support of Roquette Frères, S.A.'s Brief in Support of its Motion for Summary Judgment of Solazyme, Inc.'s Claim for Misappropriation of Trade Secrets, *Roquette Frères, S.A.* v. *Solazyme, Inc.*, C.A. No. 14-01442, District Court for the District of Delaware, D.I. 112-2, Jun. 22, 2015; Declaration of Jeffrey M. Goehring in Support of Roquette Frères, S.A.'s Brief in Support of its Motion for Summary Judgment of Solazyme, Inc.'s Claim for Misappropriation of Trade Secrets, *Roquette Frères, S.A.* v. *Solazyme, Inc.*, C.A. No. 14-01442, District Court for the District of Delaware, D.I. 112, Jun. 22, 2015; Roquette Frères, S.A.'s Opening Brief in Support of its Motion for Summary Judgment of Solazyme, Inc.'s Claim for Misappropriation of Trade Secrets, *Roquette Frères, S.A.* v. *Solazyme, Inc.*, C.A. No. 14-01442, District Court for the District of Delaware, D.I. 140, Jun. 22, 2015, Redacted Version.
Letter dated Nov. 2, 2015, from Jeffrey M. Goehring of Young & Thompson International Patent & Trademark Law (counsel for Roquette Frères, S.A.) to Gerald Suh of Solazyme, Inc., and R. James Balls and William E. McShane of Novak Druce Connolly Bove + Quigg LLP (counsel for Solazyme Roquette Nutritionals, LLC), which included the same enclosures included with the letter dated Oct. 6, 2015 of Cite No. CB.
Email dated Nov. 4, 2015, from Jeffrey M. Goehring of Young & Thompson International Patent & Trademark Law (counsel for Roquette Frères, S.A.) to Gerald Suh of Solazyme, Inc., and R. James Balls and William E. McShane of Novak Druce Connolly Bove + Quigg LLP (counsel for Solazyme Roquette Nutritionals, LLC).
Opinion dated Dec. 21, 2015 in *Roquette Frères, S.A.*, v. *Solazyme, Inc.*, Case No. 1:14-cv-01442 (D. Del. 2015) granting Solazyme's motion for an order confirming the arbitration award rendered by CPR International Institute for Conflict Prevention & Resolution on Feb. 19, 2015, in favor of Solazyme, Inc.
Youzhi Jiagong, (Jun. 8, 2007), "Oil Processing Technology (2nd edition)", Chemical Undustry Press, Title page, Publication Page, Table of Contents, pp. 206-213, (in Chinese).
"Linoleic acid and α-linolenic acid are real essential fatty acids", (Mar. 1998), Title page, Publication Page, Table of Contents, Chapter 2: Essential Fatty Acids (pp. 12-13) and Chapter 15: Selection of the most suitable fatty acids (pp. 89-91), with English translation.
Bowman, Barbara A. and Robert M. Russell (eds.), "Present Knowledge in Nutrition" (1st Edition), (Oct. 2004), Title page, Publication Page, Table of Contents, p. 231 (in Chinese).
"Auxenochlorella", article from Wikipedia, Retrieved from the Internet on Mar. 23, 2016, "https://en.wikipedia.org/w/index.php?title=Auxenochlorella&oldid=711518993".
Clore, G.M. and E.M. Chance, A computer analysis of cyanide stimulated oxygen uptake in *Chlorella protothecoides*. (Jul. 1977) FEBS Lett. 79 (2):353-356.
"Algen—Nudein ais Altmark Spezialitat (Algae noodles: a speciality from Altmark region)" in German language, and other *Chlorella* Food products, (Oct. 9, 2007), 3 pages.

IMAI, Ichiro, et al. "Advanced research on Shellfish poisonings: Current Status and overview", Table of Contents, Chapters 1 and Chapter 4, 11 pages.
"Aoko's toxin", Aichi Prefectural Institute of Public Health, 6 pages. [Retreived from the Internet Oct. 13, 2016: <URL: http://www.pref.aichi.jp/eiseiken/5f/bloom_t.html].
Lee, Yuan-Kun, "Commercial Production of microalgae in the Asia-Pacific rim", Journal of Applied Phycology, 9:403-411, (Oct. 29, 1997).
Kay, Robert A., "Microalgae as Food and Supplement", Critical Reviews in Food Sciense and Nutrition, 30(6):555-573 (Feb. 1991).
Usuki, Riichiro and Luniko Kamata,"Experimental Trials on the Role of Lipids in Good Taste and Good Body of Foods", Research reports of Shokei Gakuin College 53, May 2006, p. 85-90 (in Japanese with English Abstract).
"Chlorella Photosynthesis—Dictionary", last modified Mar. 23, 2015, Retrevied from the Internet: <URL: (http://photosyn.jp/pwiki/index.php?%E3%82%AF%E3%83%AD%E3%83%AC%E3%83%A9) with English Machine Translation.
Hirashima, Ryuta, "Framework of evaluation on inventive step requirement and significance of 'technical problem'", Patent 2010, 63(5): 34-49 (in Japanese; no translation).
Ullmann, Jorg, "The Difference between *Chlorella vulgaris*and *Chlorella pyrenoidosa*", (2006) (http://www.algomed.de/index.php?op=algenfarm_geschichte).
"History of the algae farm: Chlorella Algae—Roquette Klötze GmbH", [Retreived from the Internet Nov. 25, 2016: <URL: (http://www.algomed.de/index.php?op=algenfarm_geschichte)].
Kirk, J. et al., "Mastitis Control Program for Prototheca Mastitis in Dairy Cows", 6 pages. <<URL: milkquality.wisc.edu/wp=content/uploads/2011/09/mastitis-control-program_prototheca-mastitis.pdf>>.
Oral Summary, dated Nov. 7, 2016, for Invalidation Hearing for Japanese Patent No. 5731982 (in Chinese).
Oral Summary by the Patentee, dated Nov. 29, 2016, for Invalidation Hearing for Japanese Patent No. 5731982 (in Chinese).
USDA National Nutriet Database (https://ndb.nal.usda.gov/ndb/).
Environmental Stresses in Non Mammalian Organisms, p. 29. with English translation.
Letter from Ray Matulka to Paulette Gaynor and Sylvester Mosley, dated Apr. 18, 2013, re: Request to Cease Evaluation of Grn 000450, Letter from Ray Matulka to Paulette Gaynor, dated Apr. 18, 2013, re: High Lipid Chlorella protothecoides S106 Flour GRAS Notification and GRAS Exemption Claim (dated Apr. 18, 2013).
Solazyme Market and Products, (2005).
Letter from Susan Cho to Susan Carlson, dated Jul. 25, 2011 and "RFI's Chlorella vulgaris GRAS Self affirmation (dated Jul. 16, 2010)."
[Retreived from the Internet Oct. 13, 2016: <URL: http://hfnet.nih.go.jp/contents/detail105.htm] (in Chinese).
"Roquestte Freres, S.A. and Solazyme, Inc. Agree to Dissolve Microalgae Join Venture", (Jun. 24, 2013) Press Release, Lestrem, France.
Standard Tables of Food Composition in Japan 2015 (Seventh Revised Edition), Table of Fatty Acid Composition, Edited by the Council for Science and Technology, the Ministry of Education, Culture, Sports, Science and Technology, (available from http://www.mext.go.jp/a_menu/syokuhinseibun/1365295.htm) [Retreived from the Internet Oct. 12, 2016: <URL: (http://www.algomed.de/index.php?op=algenfarm_geschichte)]http://www.geocities.jp/jr2bvb/syokuhin/sibousan/oil_s.htm].
"'Taste' of Lipids?" [retreived from the Internet Oct. 12, 2016: <URL: (https://sites.google.com/site/coffeetambe/coffeescience/physiology/taste/fat] with English Machine Translation.
Japanese Laid-Open Publication No. 2000-175680 (translator's note: an English language member of the same patent family: EP 1142985 (A1)).
Japanese Laid-Open Publication No. 2002-223787 (translator's note: no English language counterpart could be located).
http://mcc.nies.go.jp/strainList.do?strainId=2555&condition=Auxenochlorella+protothecoides.
http://mcc.nies.go.jp/strainList.do?strainId=2568&condition=Auxenochlorella+protothecoides.

(56) References Cited

OTHER PUBLICATIONS

*Roquette Freres S.A.* v. *Solazyme Inc.*, Delaware District Court, Case No. 1:14-cv-01442 District Judge Sue L. Robinson, presiding, Solazyme, Inc.'s Answer to Plantiff Roquette Freres, S.A.'s Complaint, Petition to Confirm Arbitration Award and Counterclaims, filed Feb. 26, 2015, 29 pages.
Joint Venture and Operating agreement of Solazyme Roquette Nutritionals, LLC., dated Nov. 7, 2015.
*Solazyme, Inc.* vs. *Roquette Freres, S.A.*, Arbitration Award, dated Feb. 19, 2015.
Request for Invalidation, dated Jan. 7, 2015, for Chinese Patent Application No. 200980149978.1, 21 pages (in Chinese).
Supplemental Statement for Request for Invalidation, dated Dec. 2, 2015, for Chinese Patent Application No. 200980149978.1, 35 pages (in Chinese), including the list of submitted Counter Evidences on p. 1-2.
Notification of Acceptance of Request for Invalidation, dated Jan. 28, 2016, for Chinese Patent Application No. 200980149978.1, 4 pages (in Chinese).
Documents filed by the Petitioner—Part II, dated Apr. 29, 2015, for Chinese Patent Application No. 200980149978.1, 21 pages (in Chinese), including : Jia, Xuan, et al., "Removal of Total nitrogen form wastewater dischrage from a chemical pertilizer plant by Chlorella protothecoides USTB-01", Chinese Journal of Environmental Engineering, (Apr. 2010), 4(4):737-740 (in Chinese).
Documents filed by the Petitioner—Part III, dated May 5, 2015, for Chinese Patent Application No. 2009801499781, 21 pages (in Chinese), including :, including : Singelton Paul and Diana Sainsbury, "Dictionary of Microbiological and Molecular Biology, (3rd Ed. 2006)", pp. 155 (and Chinese translation thereof)—Singelton Paul and Diana Sainsbury, "Dictionary of Microbiological and Molecular Biology, (2nd Ed. 1987)", pp. 178-179 (and Chinese translation therof).
Statement of Grounds & Particulars of Opposition, Grounds for Opposition, In the matter of Australian Patent Application No. 2009303354 in the name of Solazyme, Inc. and Opposition by *Roquette Frères, S.A.* v. *Solazyme, Inc.*, Commonweath of Ausralia, Mar. 3, 2016, (21 pages).
Declaration of Michael Armin Borowitzka in the matter of Australian Patent Application No. 2009303354 in the name of Solazyme, Inc. And Opposition by *Roquette Frères, S.A.* v. *Solazyme, Inc.*, Commonweath of Ausralia, Jun. 2, 2016, (32 pages).
Exhibit MB-1, Federal Court of Australia, Practice Note CM7, Expert Witnesses in Proceedings on the Federal Court of Australia, commenes Jun. 4, 2013; Exhibit MB-2, Michael Armin Borowitzka Curriculum Vitae; Exhibit MB-3, J. M. Hundley, R. B. Ing and R. W. Krauss, "Algae as Sources of Lysine and Threonine in Supplementing Wheat and Bread Diets", Science, New Series, Vol. 124, No. 3221 (Sep. 21, 1956), pp. 536-537.; Exhibit MB-4, Krauss, Robert W., "Mass Culture of Algae for Food and Other Organic Compounds," American Journal of Botany, vol. 49, No. 4 (Apr. 1962), pp. 425-435.; Exhibit MB-6, Soong, Pinnan, "Productions and Development of *Chlorella* and *Spirulina* in Taiwan", *Algae Biomass: Production and Use*, Gedaliah Shelef and Carl J. Soeder (eds.), North-Holland Biomedical Press, (Dec. 1980), pp. 97-113 and title and copyright page.; Exhibit MB-7, Kawaguchi, Kotaro, "Microalgae Production Systems in Asia", *Algae Biomass: Production and Use*, Gedaliah Shelef and Carl J. Soeder (eds.), North-Holland Biomedical Press, (Dec. 1980), pp. 25-33 and title and copyright page.; Exhibit MB-8, Kay, Robert A., "Microalgae as Food and Supplement", Critical Reviews in Food Sciense and Nutrition, 30(6):555-573 (Feb. 1991).; Exhibit MB-9, Raymundo et al., "Fat mimetic capacity of Chlorella vulgaris biomass in oil-in-water food emulsions stabilized by pea protein," Food Research International, 38:961-965, (Feb. 25, 2005).; Exhibit MB-10, Samejima, H. and J Myers, "On the Heterotrophic Growth of Chlorella *pyrenoidosa*", J. Gen Microbiol, (1958), 18:107-117.
Exhibit MB-11, Aoki, Shigeji and Eiji Hase, "De- and Re-Generation of Chloroplasts in the Cells of Chlorella Protothecoides", Plant & Cell Physiol, (Sep. 5, 1964), vol. 5, pp. 473-484 [Retreived from the internet on Jun. 7, 2013 from http://pcp.oxfordjournals.org/ by Reprints Desk ].; Exhibit MB-12, Becker, E.W., "Micro-algae as a source of protein," Biotechnology Advances, 25:207-201, (Mar.-Apr. 2007).; Exhibit MB-13, Iwamoto, Hiroaki, "Industrial Production of Microalgal Cell-mass and Secondary Products—Major Industrial Species Chlorella", Chapter 11, Handbook of Microalgal Culture: Biotechnology and Applied Phycology, Amos Richmond (eds), (Dec. 1, 2003), pp. 255-263.; Exhibit MB-14, Petkov et al., "Which are fatty acids of the green alga Chlorella?," Biochemical Systematics and Ecology, 35:281-285, (2007).; Exhibit MB-15, Gladu, Patricia K., et al. "Sterol, Fatty Acid and Pigment Characteristics of UTEX 2341, a Marine Eustigmatophyte Identified Preivously as Chlorella Minutissuma (Chlorophyceae)" J. Phycol., (Jun. 21, 1995), 31:774-777.; Exhibit MB-16, Xu et al., "High Quality Biodiesel Production From a Microalga Chlorella Protothecoides by Heterotrophic Growth in Fermenters," Journal of Biotechnology, 126(4):499-507, (May 2006).; Exhibit MB-17, Matsuka et al., "Changes in Contents of Carbohydrate and Fatty Acid in the Cells of Chlorella Protothecoidesduring the process of De- and Re-Generation of Chloroplasts," Plant and Cell Physiol., 7:651-662 (Sep. 24, 1966).; Exhibit MB-18, Xuan, J. et al., "Removal of total nitrogen from wastewater discharge from a chemical fertilizer plant by Chlorela protothecoides USTB-01", Chinese Journal of Environmental Engineering, (Apr. 2010), vol. 4, No. 4, pp. 737-740.
Exhibit MB-19, Australian Application No. 2009303354B2 from International Patent Application No. PCT/US2009/060692, naming Solazyme, Inc., International Patent Publication No. 2010/045368, dated Apr. 22, 2010.; Exhibit MB-20, Pabst, W., "Nutritional evaluation of nonsewage microalgae by the rat balance method," Arch. HyrobioL Beih, (Dec. 1978), pp. 65-70; Exhibit MB-21, Urano, et al., "Effect of Osmotic Stabilizers on Protoplast Generation on Chlorella ellipsoidea Yellow/White Color Mutants", Journal of Bioscience and Bioengineering, vol. 90, No. 5, 567-569, (2000).; Exhibit MB-22, Kamiya, "Effects of Blue Light and Ammonia on Nitrogen Metabolism in a Colorless Mutant of Chlorella", Plant Cell Phyiol., 30(4):513-521 (1989); Exhibit MB-23, Biello et al., "Biofuel of the Future: Oil from Algae," Scientific American, 2 pages, (Jan. 9, 2008).
Evidence in Support, In the matter of Australian Patent Application No. 2009303354 in the name of Solazyme, Inc. and Opposition by *Roquette Frères, S.A.* v. *Solazyme, Inc.*, Commonweath of Australia, Jun. 3, 2016, (1 page).
Declaration of Young J. Suh in the matter of Australian Patent Application No. 2009303354 in the name of Solazyme, Inc. And Opposition by *Roquette Frères, S.A.* v. *Solazyme, Inc.*, Commonweath of Ausralia, Aug. 31, 2016, (94 pages); Exhibit YS1, Arbitration Award, *Solazyme Inc.* vs. *Roquette Frères*, Case 1:14-cv-01442-SLR, Document 153, Filed Dec. 21, 2015; Exhibit YS2, French Patent Publication No. FR 2 924 126, filed Nov. 28, 2007.; Exhibit YS3, Memorandum Opinion, Document 153, *Roquette Frères, S.A.* vs. *Solazyme Inc.*, Case 1:14-cv-01442-SLR, filed Dec. 21, 2015.
Declaration of Craig Patch in the matter of Australian Patent Application No. 2009303354 in the name of Solazyme, Inc. and Opposition by *Roquette Frères, S.A.* v. *Solazyme, Inc.*, Commonweath of Ausralia, Sep. 5, 2016, (22 pages); Exhibit CP-1, Federal Court of Australia, Practice Note CM7, Expert Witnesses in Proceedings on the Federal Court of Australia, commenes Jun. 4, 2013.; Exhibit CP-2, Craig Patch Curriculum Vitae.
Declaration of Craig Patch in the matter of Australian Patent Application No. 2009303354 in the name of Solazyme, Inc. and Opposition by *Roquette Frères, S.A.* v. *Solazyme, Inc.*, Commonweath of Ausralia, Sep. 28, 2016, (42 pages).; Exhibit CP3, Record of Views Formed in Response to Inquires, updated Mar. 2015 (20 pages); Exhibit CP4, Huss, V.A.R., et al., "Biochemical Taxonomy and Molecular Phylogeny of the Genus Chlorella Sensu Lato (Chlorophyta)1", J. Phycol. 35, 587-598 (Jan. 15, 1999).
Evidence in Answer, In the matter of Australian Patent Application No. 2009303354 in the name of Solazyme, Inc. and Opposition by *Roquette Frères, S.A.* v. *Solazyme, Inc.*, Commonweath of Australia, Sep. 29, 2016, (1 page).
Declaration of Michael Armin Borowitzka In the matter of Australian Patent Application No. 2009303354 in the name of Solazyme,

(56) References Cited

OTHER PUBLICATIONS

Inc. and Opposition by *Roquette Frères, S.A.* v. *Solazyme, Inc.*, Commonweath of Ausralia, Dec. 21, 2016, (14 pages).
Evidence in Reply, In the matter of Australian Patent Application No. 2009303354 in the name of Solazyme, Inc. and Opposition by *Roquette Frères, S.A.* v. *Solazyme, Inc.*, Commonweath of Ausralia, Dec. 23, 2016, (1 page).
"Roquette's Microalgae High Lipid Algal Flour Wins Most Innovative Food Ingredient at the 2013 Fi Europe Excellence Award," www.PRnewswire.com/news-release/roquettes-migroalgae-high-lipid-algal-flour-wins-most-innovative-food-ingrediant-at-the-2013-fi-europe-excellence-awards, (Nov. 25, 2013), pp. 1-5.
Freshwater Algae Culture Collection at the Institute of Hydrobiology (FACHB-collection), certification letter by the Chinse Academy of Science, "Chlorella vulgaris", (No Date).
Zhou, Lian-ning et al. "Effects of Environmental Factors on Nitrogen and Phosphorus Removal by *Chlorella vularis* in Wastewater", Current Biotechnology, (Jan. 25, 2015), vol. 5, No. 1, Title page, Publication page, Table of Contents (I Chinese and English), pp. 60-65, with English abstract.
Evidence 1, Explanation paper, filed with IP High Court Case No. H29 (gyo-ke) 10149 on Oct. 6, 2017 in Invalidation Appeal No. 2016-800012 against Japanese Patent No. 5731982, with English translation.
First Statement, Substantive Brief, filed with IP High Court Case No. H29 (gyo-ke) 10149 on Nov. 17, 2017 in Invalidation Appeal No. 2016-800012 against Japanese Patent No. 5731982, with English translation.
Second Statement, Substantive Brief, filed with IP High Court Case No. H29 (gyo-ke) 10149 on Jan. 17, 2018 in Invalidation Appeal No. 2016-800012 against Japanese Patent No. 5731982. With Explanation Paper for the Evidence. Japanese Only.
Opponent'S Outline of Submissions, in the Matter of Australian Patent Application No. 2009303354 in the name of Corbion Biotech, Inc., dated Jan. 24, 2018, 48 pages.
Response to Reg 5.23 Request, in the Matter of Australian Patent Application No. 2009303354 in the name of Corbion Biotech, Inc., filed Feb. 5, 2018, 18 pages.; Letter from David Sieveking, dated Jan. 24, 2018; Statutory Declaration of Dr Daniel Peter Sieveking, dated Jan. 24, 2018.; Exhibit DS-1, Kyle, David, "Production and Use of Lipids from Microalgae", Microalgal Lipids, Lipid Technology, (May-Jun. 1992), pp. 59-64.; Exhibit DK-2, Chen et al., "High cell density culture of microalgae in heterotrophic growth," Trends in Biotechnology, 14:421-426, (1996).
"Chlorella—Chlorella Powder—Nuts.com", [Retreived from the Internet May 2, 2016: <URL: (https://nuts.com/cookingbaking/powders/chlorella/powder.html)].
"Solazyme locates new Whole Algalin Flour project in France", (Oct. 25, 2011), http://www.biofuelsdigest.com/bdigest/2011/10/25/solazyme-locates-new-whole-algalin-flour-project-in-france/.
"Solazyme Roquette Nutritionals Golden Chlorella® Omega to be key ingredient in Natural Vitality Release of new 30oz Bottle for Energy28", (Mar 10, 2011), http://investors.terravia.com/releasedetail.cfm?releaseid=588870.
"Algae in More Bread, the Algae in Lake BreadTM," www.meerbrood. com, 3 pages, (2012). [Retreived from the Internet May 20, 2013: <URL: http://www.meerbrood.com/algen/>]. (machine translation).
Aoki, Shigeji and Eiji Hase, "De- and Re-Generation of Chloroplasts in the Cells of *Chlorella protothecoides*", Plant & Cell Physiol, (Sep. 5, 1964), vol. 5, pp. 473-484 [Retreived from the internet on Jun. 7, 2013 from http://pcp.oxfordjournals.org/ by Reprints Desk ].
Batista et al., "Microalgae bioactive components for innovative food products development," 37th WEFTA Meeting Book of Abstracts, INRB/IPIMAR, Abstract S3.14, p. 134, (2007).
Batista et al., "Novel foods with microalgal ingredients—Effect of gel setting conditions on the linear viscoelaaticity of Spirulina and Haematococcus gels," Journal of Food Engineering, vol. 110 (May 2012), pp. 182-189, http://www.sciencedirect.com/science/article/pii/S0260877411003001.
Becker, E.W., "Micro-algae as a source of protein," Biotechnology Advances, 25:207-201, (Mar.-Apr. 2007).
Belasco, Warren, "Algae Burgers for a Hungry World? The Rise and Fall of Chlorella Cuisine," Technology and Culture, 38(3):608-634, (1997).
Biello et al., "Biofuel of the Future: Oil from Algae," Scientific American, 4 pages, (Jan. 9, 2008). [Retrieved from the Internet Mar. 9, 2015: <URL: http://www.scientificamerican.com/article/biofuel-of-the-future/>].
Borowitzka, Michael A., "Microalgae as sources of pharmaceuticals and other biologically active compounds", Journal of Applied Phycology, (Feb. 1995), vol. 7, Issue 1, pp. 3-15.
Brown et al., "The amino-acid and sugar composition of 16 species of micralgae used in mariculture," J. Exp. Mar. Biol. Ecol. 145:79-99 abstract (1991).
Curtain, "Plant Biotechnology—The growth of Australia's algal b-carotene industry," *Australasian Biotech*. 10(3):19-23 (2000). [Retrieved from the Internet Apr. 5, 2010:<http://www.bioline.org. br/request?au00032>].
Day, Al. et al., "Safety evaluation of a high-lipid algal biomass from Chlorella protorhecoides," Regulatory Toxicology and Pharmacology, (Nov. 2009), 55(2): 166-180, doi:10.1016/j.yrtph.2009.06.014, 15 pages, (2009).
Derner, Roberto Bianchini et al., "Microalgas, produtos e aplicações" Cienc. Rural vol. 36 No. 6 Santa Maria Nov. 2006/Dec., with English Machien Translation.
Donhowe, R.W. et al., "Determination of Ice Crystal Size Disribution in Frozen Desserts," Journal of Dairy Sciences, (May 3, 1991), 74:3334-3344.
El-Sheekh et al., "Variation of Some Nutritional Constituents and Fatty Acid Profiles of Chlorella vulgaris Beijerinck Grown under Auto and Heterotrophic Conditions," International Journal of Botany, 5(2):153-159, (2009).
Fang et al., "On Measurement of Food Powder Reconstitution Properties," Drying Technology, 26:3-14, (2008).
Fernandez-Reiriz et al., "Biomass Production and Variation in the Biochemical Profile (Total Protein, Carbohydrates, RNA, Lipids and Fatty Acids) of Seven Species of Marine Microalgae," Aquaculture, 83:17-37, (1989).
Fradique et al., "Incorporation of Chlorella vulgaris and Spirulinamaxima biomass in pasta products. Part 1: Preparation and evaluation", Journal of the Science of Food and Agriculture, (May 13, 2010), vol. 90., Iss. 10, pp. 1656-1664.
Fradique et al., "Microalgae biomass incorporation in pasta products," 5th Pigments in Food congress—for quality and health, ISBN 978-952-10-4846-3, p. 182, (Aug. 2008). Abstract.
Gouveia et al., "Chlorella vulgaris and Haematococcus pluvialis biomass as colouring and antioxidant in food emulsions," Eur Food Res Technol, 222:362-367, (2006).
Gouveia et al., "Microalgae in Novel Food Products," Food Chemistry Research Developments, Chapter 2, Nova Science Publishers, Inc., ISBN 978-1-60456-262-0, 37 pages, (May 2008).
Gouveia et al., "Microalgal biomass as a sustainable alternative raw material," Argo Food Industry Hi-Tech, Teknoscience, 7(3):29-34, (Jan. 1, 1996).
Grima et al., "Recovery of Microalgal Biomass and Metabolites: Process Options and Economics", Biotechnology Advances, (2003) 20:491-515.
Guil-Guerrero et al., "Functional properties of the biomass of three microalgal ,"Journal of Food Engineering, 65(4):511-517, (Dec. 1, 2004).
Hase et al., "Nutritional Control of Cell Pigmentation in Chlorella Protothecoides With Special Reference to the Degeneration of Chloroplast Induced by Glucose," Plant and Cell Physiology, 5(2):227-240 (1964), [online abstract], Retrieved on Jun. 3, 2010 from http://pcp.oxfordjounals.org/cgi/content/abstract/5/2/227.
Hidaka et al., "A Hot Water Extract of Chlorella pyrenoidosa Reduces Body Weight and Serum Lipids in Ovariectomized Rats," Phytotherapy Research, 18:164-168, (2004).
Hörtensteiner et al., "Chlorophyll breakdown in Chlorella protothecoides: characterization of degreening and cloning of degreening-related genes," Plant Molecular Biology, 42:439-450, (2000).

(56) References Cited

OTHER PUBLICATIONS

Huntingdon Research Center, "Acute Oral Toxicity to Rats of Green Chlorella and Yellow Chlorella Powders," Huntingdon Research Centre, Huntingdon, England, 5 pages, (1972).
Huss, V. A. R., et al., Biochemical Taxonomy and Molecular Phylogeny of the Genus Chlorella Sensu Lato (Chlorophyta). Journal of Phycology, (Jan. 15, 1999), 35: 587-598. doi:10.1046/j.1529-8817.1999.3530587.x.
Huss et al., "Deoxyribonucleic acid reassociation in the taxonomy of the genus Chlorella," Arch Microbiol, 150:509-511, (1988).
Jong-Yuh et al., "Potential hypoglycemic effects of Chlorella in streptozotocin-induced diabetic mice," Life Sciences, 77:980-990 (2005).
Kanellos, "Algae: Another way to grow edible oils," CNET News, 6 pages, (Jan. 25, 2008). [Retrieved from the Internet Mar. 9, 2015: <URL: http://news.cnet.com/Algae-Another-way-to-grow-edible-oils/2100-11395_3-6227572.html?tag=nefd.lede>].
Kihlberg et al., "Nutritive Value, Effect," The Microbe as a Source of Food, Department of Applied Microbiology, Karolinska Institutet, Stockholm, Sweden, page 440, (1972).
Kingman, Mariah, "Algal Flour Chocolate Chip Coconut Cookies", (Sep. 18, 2011), http://www.algaecompetition.com/PDF.cfm/3food/3133.pdf.
Kirchhoff et al., "Quantitation of Odor-Active Compounds in Rye Flour and Rye Sourdough Using Stable Isotope Dilution Assays," Journal of Aricultural and Food Chemistry, (Aug. 15, 2002), vol. 50, pp. 5378-5385.
Krauss, Robert W., "Mass Culture of Algae for Food and Other Organic Compounds," American Journal of Botany, vol. 49, No. 4 (Apr. 1962), pp. 425-435.
Krüger, "Kurze Charakteristik einiger niedrerer Organismen im Saftfluss der Laubbäume," Hedwigia, 33: 241-266, (1894). Machine Translation.
Kyle, David, "Production and Use of Lipids from Microalgae", *Microalgal Lipids*, Lipid Technology, (May-Jun. 1992), pp. 59-64.
La Scala et al., "The effect of fatty acid composition on the acrylation kinetics of epoxidized triacylglycerols," Journal of the American Oil Chemists' Society, 79(1):59-63, (2002).
Lane, Jim, "The Great Algae Robbery", Biofuels Digest, (Feb. 27, 2015), dowloaded from the internet Jun. 13, 2016, 13 Pages. http://www.biofuelsdigest.com/bdigest/2015/02/27/the-great-algae-robbery/.
Lahaye, "Marine Algae as Sources of Fibres: Determination of Soluble and Incoluble Dietary Fibre Contents in Some 'Sea Vegetables'," *J. Sci. Food Agric.* 54:587-594 (1991).
Leema et al., "Heterotrophic Production of Lutein and Biomass by Chlorella Vulgaris with Different Nitrogen Sources," Algae Biofuel, Studium Press (India) Pvt. Ltd., pp. 91-101, (2011).
S. Leeson, L. Caston, and T. Maclaurin, "Organoleptic Evaluation of Eggs Produced by Laying Hens Fed Diets Containing Graded Levels of Flaxseed and Vitamin E", Poultry Science, (Apr. 22 1998), 77:1436-1440.
Leon-Banares et al., "Transgenic microalgae as green cell-factories," Trends in Biotechnology, 22(1):45-52, (2004).
Li et al., "Isolation and Purification of Lutein from the Microalga Chlorella vulgaris by Extraction after Saponification," J. Agric. Food Chem., 50(5):1070-1072, (2002).
Liang et al., "Current microalgal health food R&D activities in China", *Hydrobiologia* 512:45-48, (2004).
Marshall et al., "Ice Cream", (Aug. 31, 2000), Aspen Publishers, Gaithersburg, MD, USA, pp. 22-31, 24-35, 46-47, 58 and 262-267.
Matsuka et al., "Changes in Contents of Carbohydrate and Fatty Acid in the Cells of *Chlorella protothecoides* during the process of De- and Re-Generation of Chloroplasts," Plant and Cell Physiol., 7:651-662 (Sep. 24, 1966).
Matsuka et al., "The Role of Respiration & Photosynthesis in the Chloroplast Regeneration in the Glucose-Bleached Cells of Chlorella Protothecoides," Plant and Cell Physiol., 7:149-162 (1966).
Miao et al., "Biodiesel Production From Heterotrophic Microalgal Oil," Biosource Technology, 97(06):841-846, (2006).
Miao et al., "High Yield Bio-Oil Production from Fast Pyrolysis by Metabolic Controlling of Chlorella Protothecoides," J. Biotech., 110:85-93, (2004).
Milner, Harlod W. "The Chemical Composition of Algea", Chapter 19, Algal Culture, (1953), pp. 285-302.
Misurcova, L. et al., "Health Benefits of Algal Polysaccharides in Human Nutririon" (Abstract Only), (Aug. 18, 2012), *Adv Food Nutr Res.*, 2012;66:75-145. doi: 10.1016/B978-0-12-394597-6.00003-3.
Mitsuda et al., "Properties of Chlorella cells grown under various photo-heterotrophic conditions," Plant & Cell Physiol, 11:281-292, (1970).
Mitsuda et al., "Protein Isolates From Chlorella Algae, Torula Yeasts, and Hydrocarbon-Assimilating Microorganisms," Nutr. Sci. Vitaminol., 19:1-13, (1973).
Mizoguchi et al., "Nutrigenomic Studies of Effects of Chlorella on Subjects with High-Risk Factors for Lifestyles-Related Disease," Journal of Medicinal Food, 11(3):395-404, (2008).
Murakami et al., "Lipids and Fatty Acid Compositions of Chlorella," Nihon Yuka gakkai-shi, 46(4):423-427, (1997).
Neish et al., "Carbohydrate Nutrition of Chlorella Vulgaris," Canadian Journal of Botany, 29:68-78, (1951).
O'Grady et al., "Heterotrophic growth and lipid production of Chlorella protothecoides on glycerol," Bioprocess Biosyst Eng, 34:121-125, (2011).
Ötles et al., "Fatty Acid Composition of Chlorella and Spirulina Microalgae Species," Journal of AOAC International, 84(6):1708-1714, (2001).
Patil et al., "Fatty acid composition of 12 microalgae for possible use in aquaculture feed," Aquacult Int, 15:1-9, (2007).
Petkov et al., "Which are fatty acids of the green alga Chlorella?," *Biochemical Systematics and Ecology*, 35:281-285, (2007).
Powell et al., "Algae Feeding in Humans," *J. Nutrition*, 75:7-12, (1961).
Pratoomyot et al., "Fatty acids composition of 10 microalgal species," Songklanakarin J. Sci. Technol., 27(6):1179-1187, (2005).
Proschold et al., "Portrait of a Species: Chlamydomonas reinhardtii," Genetics, 170(4):1601-1610, (2005).
Qingyu et al., "Fine Cell Structure and Biochemical Compositions of Chlorella Protothecoides after Transferring from Autotrophic to Heterotrophic Metabolism," Journal of Nanjing University, Natural Sciences Edition, 29(4):622-630, (Oct. 29, 1993). Abstract.
Radmer et al., "Commercial applications of algae: opportunities and constraints," Journal of Applied Phycology, 6:93-98, (Apr. 1, 1994).
Rasmussen, R and Michael T. Morrissey, "Marine Biotechnology for Production of Food Ingredients", Advances in Food and Nutition Reseach, vol. 52, (2007), pp. 237-292.
Ratledge, "Regulation of lipid accumulation in oleaginous microorganisms," Biochem Soc Trans., 30(Pt 6):1047-1050, 2002.
Raymundo et al., "Fat mimetic capacity of Chlorella vulgaris biomass in oil-in-water food emulsions stabilized by pea protein," Food Research International, 38:961-965, (Feb. 25, 2005).
Rhodia GPS Vanillin GPS Safety Summary, (Mar. 2011), 6 pages.
Rodriguez-Lopez et al., "Plasma-glucose and plasma-insulin in normal and alloxanized rats treated with Chlorella," Life Sciences, Part II, 10:57-60, (1971).
Ruiz et al., "Lipids accumulation in Chlorella protothecoides through mixotrophic and heterotrophic cultures for biodiesel production," New Biotechnology, 25S:S266-S266, (Sep. 1, 2009).
Running et al., "Extracellular production of L-ascorbic acid by Chlorella protothecoides, Prototheca species, and mutants of P. moriformis during aerobic culturing at low pH," Journal of Industrial Microbiology & Biotechnology, 29:93-98, (2002).
Running et al., "Heterotrophic production of ascorbic acid by microalgae", Journal of Applied Phycology, (Apr. 1994), vol. 6, Issue 2, pp. 99-104.
Sakuradani, "Studies of Metabolic Engineering of Useful Lipid-producing Microorganisms," NISR Research Grant, (2004).
Samarasinghe, Nalin, et al., "Algal cell rupture using high pressure homogenization as a prelude to oil extraction", Renewable Energy, vol. 48, Dec. 2012, pp. 300-308.
Sansawa et al., "Production of Intracellular Phytochemicals in Chlorella under Heterotrophic Conditions," Journal of Bioscience and Bioengineering, 98(6):437-444, (Jan. 1, 2004).

(56) References Cited

OTHER PUBLICATIONS

Shi et al., "Heterotrophic production of biomass and lutein by Chlorella protothecoides on various nitrogen sources," Enzyme and Microbial Technology, 27:312-318, (2000).
Shi et al., "High Yield Production of Lutein by Heterotrophic Chlorella Prototheocoides in Fed-Batch Systems," Algae and their Biotechnological Potential, Kluwer Academic Publishers, pp. 107-119, (2001).
Shi et al., "High-Yield Production of Lutein by the Green Microalga Chlorella protothecoides in Heterotrophic Fed-Batch Culture," Biotechnol. Prog., 18(4):723-727 (2002).
Shi et al., "Production and rapid extraction of lutein and the other lipid-soluble pigments from Chlorella protothecoides grown under heterotrophic and mixotrophic conditions," Nahrung, 43:109-113, (1999).
Shi, et al., "Production of biomass and lutein by Chlorella protothecoides at various glucose concentrations in heterotrophic cultures ," Process Biochemistry, 34:341-347, (1999).
Shihira-Ishikawa et al., "Nutritional Control of Cell Pigmentation in Chlorella Protothecoides With Special Reference to the Degeneration of Chloroplast Induced by Glucose," Plant and Cell Physiology, 5(2):227-240 (Jan. 1, 1964), [online abstract], Retrieved on Jun. 3, 2010 from http://pcp.oxfordjounals.org/cgi/content/abstract/5/2/227.
Spolaore et al., "Commercial Applications of Microalgae," *J. Biosci. Bioeng.* 101(2):87-96 (2006).
Sung et al., "The research on the lipid content and composition of microalgae and their impact factors," Marine Science, 12(33)122-128, (2009). (English translation of first two pages).
Szabo et al., "Saftey evaluation of a high lipid Whole Algalin Flour (WAF) from Chlorella protothecoides," RegulatoryToxicology and Pharmacology, 63:155-165 (2012).
Szabo et al., "Saftey evaluation Whole Algalin Protein (WAP) from Chlorella protothecoides," Food and Chemical Toxicology, 59:34-45 (2013).
Takashima et al., "Further Notes on the Growth and Chlorophyll Formation of Chlorella Protothecoides," Plant & Cell Physiol., 5:321-332, (1964).
Tan et al., "Fatty acid production by heterotrophic Chlorella saccharophila," Hydrobiologia, 215:13-19, (Jun. 7, 1991).
Tasaki et al., "Digestibility of Yellow Chlorella in Suckling Goat Kids,"The Japanese Journal of Zootechnical Science, 48(11):661-663, (1977).
Tsutsui, Tomomi, et al., "Effect of Seaweed Substitution on Breadmaking (I) Chlorella," Proceedings of Seitoku Junior College of Nutrition, 2004, (35), pp. 1-7.

Wei et al "Enhanced production of lutein in heterotrophic Chlorella protothecoides by oxidative stress," Sci China Ser C-Life Sci, 51(12):1088-1093, (2008).
Wu et al., "Comparative study on Liposoluble Compounds in Autotrophic and Heterotrophic Chlorella Protothecoides," Acta Botanica Sinica, 35(11):849-858, (1992).
Xiong et al., "High-density fermentation of microalga *Chlorella protothecoides* in bioreactor for microbio-diesel production," Appl. Microbiol. Biotechnol., 78:29-36, (2008).
Xu et al., "High Quality Biodiesel Production From a Microalga *Chlorella protothecoides* by Heterotrophic Growth in Fermenters," Journal of Biotechnology, (May 2006), 126(4):499-507.
Zhang et al., "A kinetic model for lutein production by the green microalga Chlorella protothecoides in heterotrophic culture," Journal of Industrial Microbiology & Biotechnology, 23:503-507, (1999).
Zhang et al., "Medicinal and Edible Resources and Biological Active Ingredients", Lianfu Chemical Industry Press, (Sep. 1, 2005), cover page, copyright page, catalog, and pp. 256-262.
Written Opinion of the Searching Authority for International Patent Application No. PCT/FR2014/051589, dated Oct. 6, 2014, pp. 1-10 (with English Translation pp. 1-15).
Callejon, R. M., et al., "Volatile and sensory profile of organic red wines produced by different selected autochthonous and commercial Saccharomyces cerevisiae strains," Analylica Chimica Acta, 2010, vol. 660, pp. 68-75.
Cha, Y. J. el al. "Volatile components in salt-fermented fish and shrimp pastes." Journal of Food Science (1995) 60: 19-24. (Year 1995).
Crisosto, C.H., et al. , "Segregation of peach and nectarine (Prunus persica (L.) Batsch) cultivars according to their Organoleptic characteristics," Postharvest Biology and Technology, 2006, vol. 29, pp. 10-18.
Das, R., et al., "Development of Electronic Nose Method for Evaluation of HDPE Flavour Characteristics, Correlated with Organoleptic Testing," Packaging Technology and Science, 2007, vol. 20, pp. 125-136.
Dupuy, H.P. et al., "Direct sampling capillary gas chromatography of volatiles in vegetable oils." JAOCS (185) 62: 1690-1693 (Year 1985).
Guil-Guerrer, J. L., et al., "Functional properties of the biomass of three microalgal species", Journal of Food Engineering, Dec. 1, 2004, vol. 65, No. 4, pp. 511-517.
Santos, J.E. R., et al., "Analysis of Volatile Organic Compounds in Virgin Coconut Oil and their Sensory Attributes ," Philippine Journal of Science, Dec. 2011 , vol. 140, No. 2, pp. 161-171.
Yamaguchi, Kenji et al., "Volatile constitunets of green tea, gyokuro." J. Agric. Food Chem. (1981) 29: 366-370 (Year 1981).
U.S. Appl. No. 15/926,899, filed Mar. 20, 2018, Amandine Druon et al.

ALMAGIN HP – analysis in suspension (with SI)

ALMAGIN HP – individual flavor values (SI)

PROTEIN-RICH MICROALGAL BIOMASS COMPOSITIONS OF OPTIMIZED SENSORY QUALITY

CROSS-REFERENCE TO RELATED APPLICATION

This application is the U.S. national stage application of International Patent Application No. PCT/FR2014/052046, filed Aug. 6, 2014.

The present invention relates to novel protein-rich compositions of biomass of microalgae of the *Chlorella* genus having an optimized sensory profile, thereby making it possible to incorporate them into food formulations without generating undesirable flavors, and also to a method for evaluating the organoleptic profile of a protein-rich composition of biomass of microalgae of the *Chlorella* genus.

PRESENTATION OF THE PRIOR ART

It is well known to those skilled in the art that chlorellae are a potential source of food, since they are rich in proteins and other essential nutrients.

They contain especially 45% of proteins, 20% of fats, 20% of carbohydrates, 5% of fibers and 10% of minerals and vitamins.

The use of biomasses of microalgae (and principally the proteins thereof) as food is being increasingly considered in the search for alternative sources to meet the increasing global demand for animal proteins (as reported by the FAO).

Moreover, the European Union has been suffering from a structural deficit in plant proteins for years now, which has amounted in recent years to more than 20 million tons of soy equivalent, currently imported from South America.

The mass production of certain protein-rich microalgae is thus envisioned as a possible way to reduce this "protein deficit".

Extensive analyses and nutritional studies have shown that these algal proteins are equivalent to conventional plant proteins, or even are of superior quality.

Nonetheless, due to the high production costs and technical difficulties in incorporating the material derived from microalgae into organoleptically acceptable food preparations, the widespread distribution of microalgal proteins is still in its infancy.

Microalgal biomasses from various species having a high percentage of proteins have been reported (see table 1 in Becker, *Biotechnology Advances* (2007), 25:207-210).

Additionally, a certain number of patent applications in the prior art, such as patent application WO 2010/045368, teach that it is possible to adjust the culturing conditions so as to further increase the protein content of the microalgal biomass.

However, when it is desired to industrially produce microalgal biomass powders from the biomass of said microalgae, considerable difficulties remain, not only from the technological point of view, but also from the point of view of the sensory profile of the compositions produced.

Indeed, while algal powders for example produced with algae photosynthetically cultured in exterior ponds or using photobioreactors are commercially available, they have a dark green color (associated with chlorophyll) and a strong, unpleasant taste.

Even formulated in food products or as nutritional supplements, these algal powders always give this visually unattractive green color to the food product or to the nutritional supplement and have an unpleasant fishy taste or the taste of seaweed.

Moreover, it is known that certain species of blue algae naturally produce odorous chemical molecules such as geosmin (trans-1,10-dimethyl-trans-9-decalol) or MIB (2-methylisoborneol), generating earthy or musty odors.

As for chlorellae, the descriptor commonly accepted in this field is the taste of "green tea", slightly similar to other green vegetable powders such as powdered green barley or powdered green wheat, the taste being attributed to its high chlorophyll content.

Their taste is usually masked only when they are mixed with vegetables with a strong taste or citrus fruit juices.

There is therefore still an unsatisfied need for compositions of biomass of microalgae of the *Chlorella* genus of suitable organoleptic quality, allowing the use thereof in more numerous and diversified food products.

SUMMARY OF THE INVENTION

The applicant company has found that it is possible to meet this need by providing protein-rich microalgal biomass compositions having an optimized sensory profile, characterized by the overall flavor value of 4 volatile organic compounds chosen from 11 specific compounds.

Thus, the present invention relates first of all to a method for determining the organoleptic quality of a protein-rich microalgal biomass composition, comprising determining the content of 11 volatile organic compounds, the 11 volatile organic compounds being pentanal, hexanal, 1-octen-3-ol, 2-pentylfuran, octanal, 3,5-octadien-2-ol (or 3-octen-2-one), 3,5-octadien-2-one, nonanal, 2-nonenal, (E,E)-2,4-nonadienal and hexanoic acid.

Preferably, the microalgal biomass comprises more than 50% proteins by dry weight of biomass and the microalgae are of the *Chlorella* genus.

Preferably, the content of each of these 11 volatile organic compounds is determined by SPME/GC, preferably by SPME/GC-MS.

Preferably, the content of each of these 11 volatile organic compounds is determined by the surface area of the chromatography peaks after SPME/GC corresponding to each of these 11 volatile organic compounds.

Preferably, the content of each of these 11 volatile organic compounds, in particular the surface area of the chromatography peaks corresponding to the 11 volatile organic compounds, is compared to that of a reference protein-rich microalgal biomass composition or compositions for which the organoleptic qualities are defined, especially as unacceptable or acceptable.

The present invention also relates to a method for defining an analytical profile of volatile organic compounds making it possible to evaluate the organoleptic quality of the protein-rich microalgal biomass compositions, comprising:
  the construction of a first matrix associating microalgal biomass compositions, including two controls of acceptable and unacceptable organoleptic quality, with the evaluation of their organoleptic qualities by a sensory panel of at least 15 individuals,
  the construction of a second matrix associating with these same compositions their characterization by a volatile organic compound analysis profile, and
  the correlation of the first matrix with the second to produce a relationship model on the basis of which the compositions having an optimized organoleptic profile can thus be characterized by their analytical profile of volatile organic compounds.

Preferably, the microalgal biomass comprises more than 50% proteins by dry weight of biomass and the microalgae are of the *Chlorella* genus.

Preferably, the descriptors of the sensory analysis comprise:
the following odors: vegetable, mash, stock, rancid butter, cheese, manure, fermented, peanut and paint; and
the following colors: yellow and green.

Finally, the present invention relates to selecting 4 of the 11 volatile organic compounds having a low olfactory threshold (that is to say having a major impact on the overall odor perceived by the members of the sensory panel), in order to construct a simplified model which makes it possible to give an overall flavor value to the protein-rich microalgal biomass compositions. Thus, the invention relates to a method for determining the organoleptic quality of a protein-rich microalgal biomass composition, comprising determining the content of 4 volatile organic compounds, these 4 organic compounds being 3,5-octadien-2-ol (or 3-octen-2-one), 1-octen-3-ol, 3,5-octadien-2-one and (E,E)-2,4-nonadienal.

This overall flavor value is then expressed as the sum of the individual flavor values of 3,5-octadien-2-ol (or 3-octen-2-one), 1-octen-3-ol, 3,5-octadien-2-one and (E,E)-2,4-nonadienal.

Preferably, the microalgal biomass comprises more than 50% proteins by dry weight of biomass and the microalgae are of the *Chlorella* genus.

The protein-rich microalgal biomass compositions in accordance with the invention thus have an optimized sensory profile when their overall flavor value is low, preferably between 0 and 40% relative to that of an organoleptically unacceptable reference microalgal flour composition.

The present invention also relates to a method for selecting protein-rich microalgal biomass compositions having an acceptable organoleptic profile, characterized in that the organoleptic quality is determined by the method as described above, and that the composition is selected when the overall flavor value calculated by the method as described above is between 0 and 40% relative to that of an organoleptically unacceptable reference microalgal biomass composition. Preferably, the microalgal biomass comprises more than 50% proteins by dry weight of biomass and the microalgae are of the *Chlorella* genus.

Preferably, the microalgae are of the *Chlorella* genus and are chosen in particular from the group consisting of *Chlorella vulgaris, Chlorella sorokiniana* and *Chlorella protothecoides*, and more particularly *Chlorella protothecoides*.

Preferably, the microalgal biomass comprises more than 50% proteins by dry weight of biomass.

DETAILED DESCRIPTION OF THE INVENTION

For the purposes of the invention, a protein-rich microalgal biomass composition has an "optimized sensory profile" or an "optimized organoleptic quality" when its evaluation by a sensory panel concludes that there is an absence of off-notes which impair the organoleptic quality of said food formulations containing these microalgal biomass compositions.

The term "organoleptic quality" is intended to mean the property of a food in terms of color and odor.

These off-notes are associated with the presence of undesirable specific odorous and/or aromatic molecules which are characterized by a perception threshold corresponding to the minimum value of the sensory stimulus required to arouse a sensation.

The "optimized sensory profile" or "optimized organoleptic quality" is then reflected by a sensory panel by obtaining the best scores on a scale of evaluation of the 2 sensory criteria (color and odors).

The term "approximately" is intended to mean the value plus or minus 10% thereof, preferably plus or minus 5% thereof. For example, "approximately 100" means between 90 and 110, preferably between 95 and 105.

The term "microalgal biomass composition" is intended to mean a composition comprising at least 50%, 60%, 70%, 80% or 90% by dry weight of microalgal biomass. However, other ingredients can optionally be included in this composition.

The term "protein-rich" is intended to mean a proteins content in the biomass of more than 50% by dry weight, preferably more than 55%, more preferably still more than 60%, 65% and 70% by dry weight of biomass.

For the purposes of the present invention, the term "microalgal biomass" should be understood in its broadest interpretation and as denoting, for example, a composition comprising a plurality of particles of microalgal biomass. The microalgal biomass is derived from whole microalgal cells.

A certain number of prior art documents, such as international patent application WO 2010/045368, describe methods for the production and use in food of protein-rich *Chlorella* microalgal biomass.

The microalgae in question in the present invention are therefore microalgae of the *Chlorella* genus, more particularly *Chlorella* protothecoides, more particularly still *Chlorella* deprived of chlorophyll pigments, by any method known per se to those skilled in the art (either because the culture is carried out in the dark, or because the strain has been mutated so as to no longer produce these pigments).

In particular, the microalgae can be chosen, non-exhaustively, from *Chlorella protothecoides, Chlorella kessleri, Chlorella minutissima, Chlorella sp., Chlorella sorokiniana, Chlorella luteoviridis, Chlorella vulgaris, Chlorella reisiglii, Chlorella ellipsoidea, Chlorella saccarophila, Parachiorella kessleri, Parachiorella Prototheca stagnora* and *Prototheca moriformis*. Thus, in one quite particular embodiment, the microalgal biomass composition is a *Chlorella* biomass composition, and in particular a *Chlorella* protothecoides biomass composition.

The fermentative process described in this patent application WO 2010/045368 thus allows the production of a certain number of microalgal biomass compositions of variable sensory quality.

The method as described in the present document therefore makes it possible to select the protein-rich microalgal biomass compositions which have an acceptable organoleptic profile, especially for food applications, without having to organize organoleptic evaluations by a panel of individuals in order to do so.

1. Definition of the Sensory Profile by Detecting 11 Volatile Organic Compounds

The applicant company has discovered that the sensory profile of a protein-rich microalgal biomass composition can be defined by the nature and the threshold of detection of odorous specific molecules, in particular of specific volatile organic compounds.

Indeed, it has identified 11 volatile organic compounds, the content of which in a protein-rich microalgal biomass composition makes it possible to determine the organoleptic quality of said composition.

These 11 volatile organic compounds are the following: pentanal, hexanal, 1-octen-3-ol, 2-pentylfuran, octanal, 3,5-octadien-2-ol (or 3-octen-2-one), 3,5-octadien-2-one, nonanal, 2-nonenal, (E,E)-2,4-nonadienal and hexanoic acid.

Thus, the present invention relates to a method for determining the organoleptic quality of a protein-rich microalgal biomass composition, comprising determining the content of each of these 11 volatile organic compounds, the 11 volatile organic compounds being pentanal, hexanal, 1-octen-3-ol, 2-pentylfuran, octanal, 3,5-octadien-2-ol (or 3-octen-2-one), 3,5-octadien-2-one, nonanal, 2-nonenal, (E,E)-2,4-nonadienal and hexanoic acid.

The method does not exclude determining the content of other volatile organic compounds. However, the 11 volatile organic compounds are sufficient to determine the organoleptic quality of a protein-rich microalgal biomass composition.

Preferably, these volatile organic compounds are sampled by solid phase microextraction (SPME) and analyzed by gas chromatography GC, in particular by GC-MS (gas chromatography-mass spectrometry).

The volatile fraction is extracted from the sample of the protein-rich microalgal biomass composition by heating said composition for a sufficient period of time in the presence of an SPME fiber.

The fiber may, for example, be chosen, non-exhaustively, from the group consisting of carboxen and polydimethylsiloxane (CAR/PDMS), divinylbenzene, carboxen and polydimethylsiloxane (DVB/CAR/PDMS), an alloy of metal and of polydimethylsiloxane (PDMS), a Carbopack-Z® fiber (graphitized carbon black), polyacrylate, Carbowax® polyethylene glycol (PEG), and PDMS/DVB.

Preferably, a DVB/CAR/PDMS fiber (df 50/30 μm) is used.

Here, the applicant company recommends using a wet extraction technique (aqueous suspension) between 40 and 70° C., preferably between 50 and 65° C., in particular approximately 60° C. for at least 10 minutes, preferably at least 15 minutes and for example between 15 minutes and 1 hour.

Preferably, this extraction step is carried out in a sealed container. A sufficient amount of sample must be used, for example at least 1 g, especially between 1 g and 10 g and in particular approximately 2 g.

These 2 g are then suspended in 7 ml water containing 1 g $CaCl_2$, 200 μl HCl and 2.32 μg hexanal-d12 (internal standard), placed in a sealed SPME flask (20 ml).

The volatile organic compounds are then desorbed at a temperature compatible with the type of SPME fiber used, for example between 220 and 250° C. for the fiber used in our tests, more precisely at 230° C., and injected into the analysis system.

Preferably, the analysis is carried out by gas chromatography GC, in particular by GC-MS.

Several GC/MS devices are commercially available, for example the GC/Mass Clarus spectrometer (PerkinElmer, USA), the Hewlett Packard 6890 gas chromatograph (Hewlett Packard, USA) and the Agilent 6890N gas chromatograph coupled to the Agilent 5973 selective mass detector.

The ionization methods which can be used in GC/MS are for example mass spectrometry with electron impact ionization (EI), chemical impact ionization (CI), electrospray ionization, luminescent discharge, field desorption (FD), etc.

The volatile substances extracted are more precisely desorbed here in the injector of the TSQ GC-MS system from Thermo Scientific, and then separated on a CPwax52 (60 m×0.25 mm, 0.25 μm) column with helium gas at 1.5 ml/min.

The temperature program is:
50° C. isotherm for 3 min, then
programming at 5° C./minute up to 230° C.,
then isotherm for 20 min.

The detection is carried out by electron impact (EI) mass spectrometry (MS) and the compounds are identified by comparison with the EI spectra of the NIST library.

Thus, the height or the surface area of the chromatography peak corresponding to the volatile organic compound correlates with the amount of said compound.

The term "surface area of the peak" is intended to mean the surface area of a specific ion under the curve in the SPME-GC/MS chromatogram.

Preferably, the content of one of the 11 volatile organic compounds is determined by the surface area of the peak of the specific ion of the SPME-GC/MS chromatogram corresponding to this volatile organic compound.

The content of volatile organic compounds is determined, especially in comparison with that of a reference product.

Thus, overall, a low total content of the 11 volatile organic compounds is associated with an optimized organoleptic quality. Conversely, a higher total content of the 11 volatile organic compounds is associated with a medium, or even poor or unacceptable, organoleptic quality.

For example, the total content of a composition with an acceptable organoleptic quality is low when it is at least two times less than that of a composition with an unacceptable organoleptic quality, for example at least 2, 3 or 4 times less, and in a most demanding embodiment, at least 10 times less.

2. Definition of the Sensory Panel and Choice of Descriptors

The present invention relates to a method for testing the organoleptic qualities of a protein-rich microalgal biomass composition comprising evaluation of the organoleptic qualities by a panel of testers. This evaluation can especially be carried out by the methods detailed below.

The applicant company also provides a method for defining an analytical profile of volatile compounds making it possible to evaluate the organoleptic quality of the microalgal biomass compositions, comprising:
the construction of a first matrix associating protein-rich microalgal biomass compositions, including preferably two controls of acceptable and unacceptable organoleptic quality, with the evaluation of their organoleptic qualities by a sensory panel of at least 15 individuals,
the construction of a second matrix associating with these same compositions their characterization by a volatile organic compound analysis profile, and
the correlation of the first matrix with the second to produce a relationship model on the basis of which the compositions having an optimized organoleptic profile can thus be characterized by their analytical profile of volatile organic compounds.

A sensory panel is formed in order to evaluate the sensory properties of various batches of microalgal biomass compositions, in particular *Chlorella protothecoides* biomass compositions.

In order to evaluate the sensory properties of the protein-rich microalgal biomass compositions, a panel of at least 15 individuals, for example 18 individuals, was brought together.

This "expert panel" makes it possible to carry out analyses of the QDA® (Quantitative Descriptive Analysis) type, conventionally referred to as "sensory profiles" (Stone, H., Sidel, J-L., Olivier, S., Woolsey, A., Singleton, R. C; (1974), Sensory evaluation by quantitative descriptive analysis, *Food Technology*, 28(11), 24-33).

As clarified by standard NF ISO 11035: 1995, sessions for generating descriptors were undertaken in order to exhaustively describe the olfactory properties of the protein-rich microalgal biomass compositions.

For this purpose, batches of protein-rich microalgal biomass compositions identified as being highly heterogeneous were placed in solution at 3% in water.

Each panelist evaluates this solution in a closed glass jar which has been heated beforehand in a water bath to 55° C., and lists all the odors he or she senses from the product.

During the sessions for generating descriptors, more than 60 terms were listed by the judges to describe the odor of the protein-rich microalgal biomass compositions.

The list of descriptors was firstly reduced qualitatively (e.g: "lawn" odor="cut grass" odor), in order to obtain a list of 16 descriptors, then some QDA® sessions enabled the list to be further reduced (cf: ISO 4121:1987) to 9 sensory descriptors.

Preferably, the reference products as presented in the following table are associated with each descriptor:

| Descriptor | Reference |
|---|---|
| vegetable | Mixed herb at 3% |
| mash | Mashed potato flakes at 5.6% |
| stock | 1 KUB OR from the company MAGGI per 2 l water |
| rancid butter | Rancid butter at 2.5% |
| cheese | Gorgonzola rind at 2% |
| manure | Manure at 2% |
| fermented | Tryptone (yeast extract) at 0.75% |
| peanut | Ground peanuts at 1.5% |
| paint | Highly oxidized protein-rich microalgal composition at 3% |

Since the "paint" descriptor was the most organoleptically discriminating, it is recommended by the applicant company to use it as the main descriptor in order to establish the sensory classification of the various batches of protein-rich microalgal biomass compositions produced.

Training the Panel

Various exercises were carried out in order to train the panel in the use of intensity scales for each descriptor (NF ISO 08587:1992, ISO 08586-1:1993, ISO 08586-2: 1994).

The performance of the panel was finally validated by carrying out a profile exercise 3 times with the same batches of protein-rich microalgal biomass compositions; since the panel was considered to be discriminating, consensual and reproducible (method described in: Pages, J., Lê, S., Husson, F., Une approche statistiques de la performance en analyse sensorielle descriptive [A statistical approach to performance in descriptive sensory analysis], *Sciences des aliments*, 26(2006), 446-469), the tool can be used for the sensory analysis of the various batches of protein-rich microalgal biomass compositions, using the QDA® method.

Sensory Profile

The panel analyses each protein-rich microalgal biomass composition one after the other on intensity scales for each descriptor.

The questionnaire for one profile session (for 1 sample) is as follows:

| Color | | | | | |
|---|---|---|---|---|---|
| light | | | | | dark |
| Yellow ☐ | ☐ | ☐ | ☐ | ☐ | ☐ |
| Green ☐ | ☐ | ☐ | ☐ | ☐ | ☐ |

| Odors | | | | | |
|---|---|---|---|---|---|
| not perceived 0 | weak 1 | quite weak 2 | medium 3 | quite strong 4 | strong 5 |
| vegetable ☐ | ☐ | ☐ | ☐ | ☐ | ☐ |
| mash ☐ | ☐ | ☐ | ☐ | ☐ | ☐ |
| stock ☐ | ☐ | ☐ | ☐ | ☐ | ☐ |
| rancid butter ☐ | ☐ | ☐ | ☐ | ☐ | ☐ |
| cheese ☐ | ☐ | ☐ | ☐ | ☐ | ☐ |
| manure ☐ | ☐ | ☐ | ☐ | ☐ | ☐ |
| fermented ☐ | ☐ | ☐ | ☐ | ☐ | ☐ |
| peanut ☐ | ☐ | ☐ | ☐ | ☐ | ☐ |
| paint ☐ | ☐ | ☐ | ☐ | ☐ | ☐ |

Analyses of variance (ANOVAs) are carried out in order to evaluate the discriminating capacity of the descriptors (descriptors of which the p-value associated with the Fisher test is less than 0.20 for the Composition effect in the model Descriptor~Composition+Panelist).

The Composition effect is interpreted as the discriminating capacity of the descriptors: if there is no effect (Critical Probability>0.20), the various batches of compositions were not discriminated according to this criterion.

The smaller the critical probability, the more discriminating the descriptor.

The paint descriptor stood out as one of the most significant descriptors for characterizing the acceptability of a batch; the grade obtained for this descriptor will serve for sensory classification.

This classification therefore then serves as a basis for studying the analytical profile of the volatile organic compounds and selecting molecules responsible for the poor organoleptic quality of the microalgal biomass compositions.

Thus, the profile of the volatile organic compounds of the microalgal biomass compositions is determined. It is determined by any method known to those skilled in the art, and preferably by SPME/GC-MS, as detailed above.

The analysis of the volatile compounds gives very complex GC-MS chromatograms, with a very large number of peaks. By means of analyses of variance and linear regressions, the volatile organic compounds which correlate best with the results obtained for the sensory matrix and with the paint odor.

Thus, an optimized organoleptic profile is associated and characterized by an analytical profile of volatile organic compounds.

In one preferred embodiment, the various organic compounds selected will be considered in terms of their total content, in comparison with reference compositions, especially as defined above. In particular, the total surface area of the chromatography peaks corresponding to the volatile organic compounds selected will be considered and compared.

3. Simplified Model Based on Four Volatile Organic Compounds Having an Impact on the Overall Odor In this preferred embodiment, the applicant company found that it is advantageously possible to establish an overall flavor value for the protein-rich microalgal biomass compositions having an optimized sensory profile, which overall value is based on 4 volatile organic compounds chosen from the 11 organic compounds identified above.

These volatile organic compounds are selected on the basis of their criterion of low olfactory threshold. The overall flavor value is then established according the relationship:

Overall flavor value=Σ☐ of the individual flavor values of 3,5-octadien-2-ol (or 3-octen-2-one), 1-octen-3-ol, 3,5-octadien-2-one and (E,E)-2,4-nonadienal.

Total FV=ΣFV(3,5-octadien-2-ol), FV(1-octen-3-ol), FV(3,5-octadien-2-one), and FV[(E,E)-2,4-nonadienal], where FV=Concentration of the compound x/olfactory threshold of the compound x As will be shown in the examples below, the protein-rich microalgal biomass compositions having a low overall flavor value of between 0 and 40%, relative to that of an organoleptically unacceptable reference microalgal biomass composition, are certain to have an optimized sensory profile.

The invention will be understood more clearly from the examples which follow, which are intended to be illustrative and nonlimiting.

EXAMPLES

Example 1. Definition of the Sensory Test

The perception of the protein-rich microalgal biomass composition is determined by solubilization in water, the neutral medium par excellence.

A sensory panel was therefore formed to evaluate, according to the methodology set out above, the sensory properties of various batches of biomass of protein-rich microalgae, prepared according to the teaching of patent application WO 2010/045368.

18 batches of microalgal biomass were tested: batch 11, batch 12, batch 14, batch 33, batch 34, batch 42, batch 43, batch 44, batch 54, batch 81, batch 82, batch 83, batch 84, batch 85, batch 92, batch 93, batch 111, batch 112.

The result of such characterization of the batches is given based on the highly characteristic descriptor of the odor of "paint".

Data Processing:

The analyses were carried out using the R software (freely sold):

R version 2.14.1 (Dec. 22, 2011)
Copyright (C) 2011 The R Foundation for Statistical Computing
ISBN 3-900051-07-0
Platform: i386-pc-mingw32/i386 (32-bit)

The software is a working environment which requires the loading of modules containing the calculation functions.

The modules used for the processing of profile data are as follows:

For the ANOVA: Package car version 2.0-12
For the Linear Regression: Package stats version 2.14-1

The ANOVA shows significantly different results from one product to the next:

Anova table (Type-III tests)
Response: Data [,paint]

|  | Sum of squared deviations from the mean | df | F value | Pr(>F) |
|---|---|---|---|---|
| (mean) | 327.94 | 1 | 234.1068 | <2.2 × 10$^{-16}$ |
| Composition | 684.40 | 17 | 28.7393 | <2.2 × 10$^{-16}$ |

-continued

Anova table (Type-III tests)
Response: Data [,paint]

|  | Sum of squared deviations from the mean | df | F value | Pr(>F) |
|---|---|---|---|---|
| Panelist | 118.84 | 19 | 4.4649 | 7.097 × 10$^{-09}$ |
| Residues | 410.44 | 293 | | |

The mean values obtained, by product, are as follows:

| Compositions | mean | standard deviation | repetition |
|---|---|---|---|
| Batch 092 | 0.00 | 0.00 | 8 |
| Batch 111 | 0.00 | 0.00 | 9 |
| Batch 12 | 0.10 | 0.10 | 10 |
| Batch 112 | 0.28 | 0.12 | 36 |
| Batch 43 | 0.29 | 0.17 | 21 |
| Batch 44 | 0.33 | 0.26 | 12 |
| Batch 33 | 0.36 | 0.36 | 11 |
| Batch 11 | 0.40 | 0.40 | 10 |
| Batch 81 | 0.96 | 0.25 | 23 |
| Batch 14 | 1.00 | 0.50 | 9 |
| Batch 82 | 1.50 | 0.34 | 24 |
| Batch 34 | 1.64 | 0.38 | 22 |
| Batch 42 | 1.96 | 0.25 | 49 |
| Batch 93 | 2.67 | 0.58 | 9 |
| Batch 84 | 3.23 | 0.36 | 22 |
| Batch 54 | 4.09 | 0.41 | 11 |
| Batch 83 | 4.24 | 0.16 | 34 |
| Batch 85 | 4.60 | 0.22 | 10 |

FIG. 1 gives the classification of the various batches in light of the grade given by the panelists based on this "paint" criterion.

The classification is thus as follows, in increasing order of "paint" grade:

batch 92>batch 111>batch 12>batch 112>batch 43>batch 44>batch 33>batch 11>batch 81>batch 14>batch 82>batch 34>batch 42>batch 93>batch 84>batch 54>batch 83>batch 85.

Batch 92 is therefore defined as the control for acceptable organoleptic quality for this paint descriptor.

Batch 85, for its part, is defined as the control for unacceptable organoleptic quality for this paint descriptor.

This organoleptic classification having now been established, it is possible, efficiently according to the invention, to analyze the SPME/GC-MS profile of these samples in order to identify the reference molecular targets that will make it possible to define the quality of the compositions produced.

Example 2. Identification of the Volatile Organic Compounds (VOCs), by SPME/GC-MS, Associated with Unacceptable "Paint Odor" Organoleptic Classifications In order to carry out the SPME/GC-MS analysis of the 18 various batches of microalgal biomass compositions, the process is carried out as indicated above in aqueous suspension.

Analysis of the Volatile Compounds on Products in Aqueous Suspension

The volatile compounds were analysed in aqueous suspension in order to reduce the matrix effect, and an internal standard was added.

Visually, as shown in FIG. 2, the GC-MS chromatograms remain very complex, with a very high number of compounds.

The first approach consists in comparing the chromatographic profiles, in integrating all the peaks between 3.2 and 35.0 min (TIC, "total ion current"), and in checking whether these "untreated" results enable a link to be made to the sensory classification.

The comparison of the chromatographic profiles and the integration of all the peaks between 3.2 and 35.0 min (TIC, "total ion current")—see FIG. 3—do not enable a link to be made to the sensory classification.

Because of the high complexity of the chromatograms, it is difficult to visually distinguish acceptable products from unacceptable products.

The integration of the surface areas of the chromatograms also does not enable a clear distinction to be made between acceptable and unacceptable products.

Moreover, this approach with untreated data does not enable it to be known which volatile compound(s) is (are) responsible for the off-notes or undesirable tastes or odors, nor to specifically monitor their appearance, nor to have any information on how they are formed.

A second approach consisted in adding to the list of volatile organic compounds of the above model by listing the volatile compounds identified on the SPME/GC-MS chromatograms which appear to accompany the organoleptic classifications.

From the GC-MS-olfactometric analysis of six samples, certain volatile compounds stood out; predominantly aldehydes derived from the degradation of the lipid fraction of the protein-rich microalgal biomass compositions, which are apparently responsible for the off-notes or undesirable tastes or odors.

In this second approach, it was thus decided to monitor some of these molecules selected by GC-MS-olfactometry and GC-MS of the various products.

In order to select the representative volatile organic compounds, a series of analyses of variance is carried out so as to keep only the volatile organic compounds which actually differ from one composition to the other given the variability of the SPME-GC/MS measurement.

The model is the following: Volatile organic compound~Composition; only the compounds for which the critical probability associated with the Fisher test is less than 0.05 are retained.

Two examples of ANOVA on the compounds 2-nonenal and 3,5-octadien-2-one are given here:

| Anova table (Type-III tests) | | | | |
|---|---|---|---|---|
| | Sum of squared deviations from the mean | df | F value | Pr(>F) |
| 2-nonenal | | | | |
| (mean) | 292.13 | 1 | 72.8516 | $3.51 \times 10^{-06}$ |
| Composition | 664.79 | 17 | 9.7522 | 0.0002394 |
| Residues | 44.11 | 11 | | |
| 3,5-Octadien-2-one (peak 2) | | | | |
| (mean) | 56344 | 1 | 20.0633 | 0.0009326 |
| Composition | 72570 | 17 | 1.5201 | 0.2424099 |
| Residues | 30891 | 11 | | |

It appears on the first volatile organic compound (2-nonenal) that the composition effect is significant (critical probability <0.00025), which means that there is a significant difference between the products given the variability of the measurement.

On the second compound (3,5-octadien-2-one, peak 2), the composition effect is not significant (critical probability >0.05). Thus, for the study, 2-nonenal will be retained but 3,5-octadien-2-one will not.

After this first selection of volatile compounds, linear regression models are established: this involves explaining the "paint" variable by each compound one by one.

As many models as there are compounds are therefore constructed. The model is the following: Paint~Compound.

In order to select the final list of compounds identified as responsible for the unacceptable organoleptic classifications (off-notes) observed, only the compounds for which the critical probability associated with Student's test is less than 0.05 (test for nullity of the linear regression coefficient) will be retained.

The $R^2$ associated with the model is an indicator for quantifying the percentage of variability explained by the compound. It may not be very high, but significant; for this reason, it is chosen to select the compounds according to the critical probability (so as not to neglect a compound which has little but significant influence on the paint odor described by the panel).

Coefficients:

| | Estimator | Std value | t value | Pr(>|t|) |
|---|---|---|---|---|
| (ordinate at the origin) | −0.669037 | 0.138335 | −4.836 | 0.000182 |
| Hexanal | 0.019196 | 0.002593 | 7.404 | $1.49 \times 10^{-06}$ |

Residual standard error: 0.4444 on 16 degrees of freedom
Multiple $R^2$: 0.7741, adjusted $R^2$: 0.76
Statistic F: 54.82 on 1 and 16 degrees of freedom, critical probability: $1.491 \times 10^{-06}$ Coefficients:

| | Estimator | Std value | t value | Pr(>|t|) |
|---|---|---|---|---|
| (ordinate at the origin) | −0.45338 | 0.24852 | −1.824 | 0.0868 |
| 3,5-octadien-2-one (peak 1) | 0.04346 | 0.01614 | 2.693 | 0.0160 |

Residual standard error: 0.7756 on 16 degrees of freedom
Multiple $R^2$: 0.3119, adjusted $R^2$: 0.2689
Statistic F: 7.252 on 1 and 16 degrees of freedom, critical probability: 0.016

For these 2 compounds, hexanal and 3,5-octadien-2-one (peak 1), the critical probability is lower than 0.05, therefore they are correlated with the paint odor described by the panel.

The 11 compounds of the study are found to be well correlated with the "paint" descriptor.

These 11 molecules selected are listed in the table below:

| | Molecule | Retention time (min) | Odor | Olfactory threshold (ppb) | Specific ion m/z |
|---|---|---|---|---|---|
| 1 | pentanal | 6.24 | Green | 18* | 44 |
| 2 | Hexanal | 8.24 | Cut grass, green apple | 4.5 | 82 |
| 3 | 1-octen-3-ol | 17.99 | Mushroom-solvent (paint), mushroom-ink | 1/0.05* | 57 |

-continued

| Molecule | Retention time (min) | Odor | Olfactory threshold (ppb) | Specific ion m/z |
|---|---|---|---|---|
| 4 2-pentylfuran | 12.10 | floral | 6 | 81 |
| 5 Octanal | 13.82 | Floral-citrus | 0.7 | 84 |
| 6 3,5-octadien-2-ol or 3-octen-2-one | 17.03 | Floral-zest | 0.1** | 111 |
| 7 3,5-octadien-2-one (2 peaks) | 19.96 + 21.24 | floral | 0.1** | 95 |
| 8 Nonanal | 16.68 | Floral-green, floral | 1 | 57 |
| 9 2-Nonenal | 20.37 | Vegetable, oil | 0.08 | 83 |
| 10 (E,E)-2,4-nonadienal | 24.42 | Oily-oxidized | 0.09 | 81 |
| 11 Hexanoic acid | 27.51 | Cheese, rancid | 3000 | 60 |

*olfactory threshold according to H. Jelen, Journal of Chromatographic Science, vol. 44, August 2006
**estimated value
Unless indicated otherwise, the olfactory threshold is taken from www.leffingwell.com/odorthre.htm As shown in FIG. 4, the unacceptable products appear to be much more loaded with these 11 volatile compounds than the acceptable samples.

The statistical analysis confirms that all 11 molecules are significant (except the second peak of 3,5-octadien-2-one at 21.24 min).

In conclusion, monitoring these 11 molecules (pentanal, hexanal, 1-octen-3-ol, 2-pentylfuran, octanal, 3,5-octadien-2-ol (or 3-octen-2-one), 3,5-octadien-2-one (first of the 2 peaks), nonanal, 2-nonenal, (E,E)-2,4-nonadienal, hexanoic acid) makes it possible to distinguish acceptable products from unacceptable products on the basis of the "paint" criterion, by analyzing the volatile substances of the product placed in aqueous suspension.

Creating the Simplified Model

In order to simplify the model, it is decided to retain the compounds having the greatest impact on the overall odor of the protein-rich microalgal biomass compositions according to the invention, that is to say the compounds with extremely low olfactory thresholds.

These individual flavor values (=concentration of the compound/olfactory threshold thereof) are represented in FIG. 5.

Taking into account the concentration and the olfactory threshold of each compound, four compounds appear to be particularly important for the sensory properties of the protein-rich microalgal biomass compositions according to the invention: 3,5-octadien-2-ol or 3-octen-2-one (floral-zest), 1-octen-3-ol (mushroom-solvent, paint, mushroom-ink), 3,5-octadien-2-one (the first of the two peaks, floral), and (E,E)-2,4-nonadienal (oily-oxidized).

The individual descriptors of these four compounds bring together very well the overall perceived odor of the unacceptable protein-rich microalgal biomass compositions according to the invention.

It is therefore possible to establish an overall flavor value for the protein-rich microalgal biomass compositions based on these four compounds:

Overall flavor value=Σ of the individual flavor values of 3,5-octadien-2-ol (or 3-octen-2-one), 1-octen-3-ol, 3,5-octadien-2-one and (E,E)-2,4-nonadienal.

As shown in FIG. 6, it is henceforth easy to classify the various batches of protein-rich microalgal biomass compositions into two families:

acceptable: these are batches 111, 92, 12, 112, 43, 33, 33, 81, 14, 44, 82 and 34;

unacceptable: these are batches 83, 84 and 85.

It should be noted that batch 85, which is a batch of organoleptically unacceptable quality according to example 1, has a flavor value of 100%.

The acceptable batches therefore do indeed have an overall flavor value of between 0 and 40% compared to that of an unacceptable reference microalgal flour composition, in this case batch 85.

Batches 42, 93 and 54 have an overall flavor value, based on the four organoleptic compounds, far greater than that of the reference batch 85.

However, it should be noted that batch 85 was defined as unacceptable on the basis solely of the "paint" descriptor.

Batches 42, 93 and 54, in terms of the analysis of volatile organic compounds, are particularly affected, undoubtedly by a synergistic effect between volatile organic compounds.

This does not detract from the fact that the simplified model based on this selection of the 4 volatile organic compounds from the reference 11 makes it possible to classify the protein-rich microalgal biomass compositions into two distinct and easily identifiable families.

Figure 1:
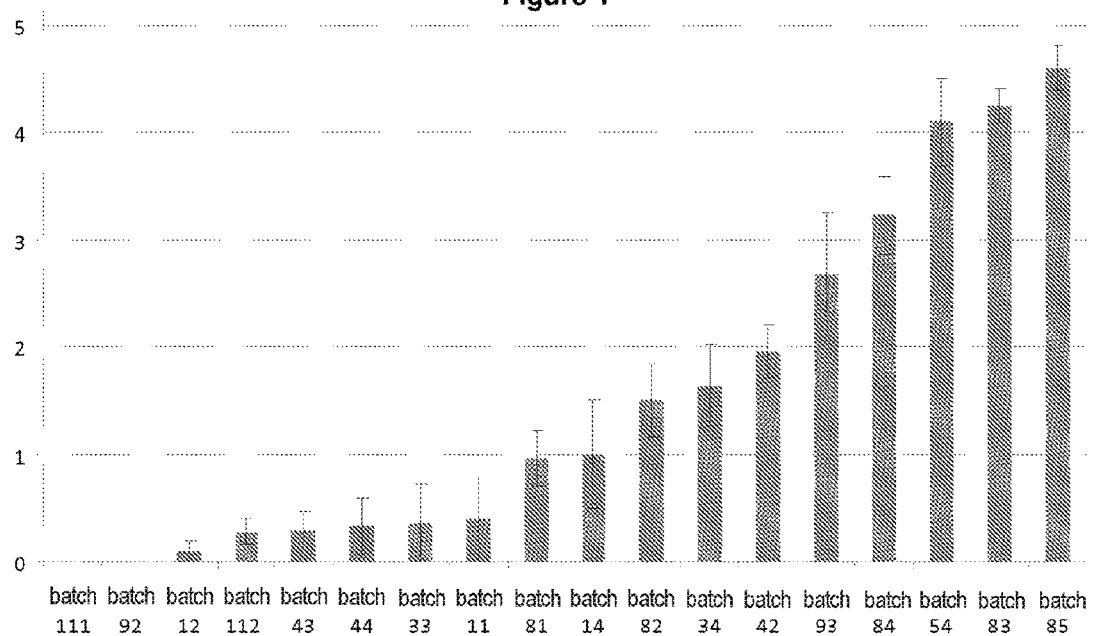
FIG. 1: Average grade obtained for the paint descriptor for each of the compositions
Figure 2:
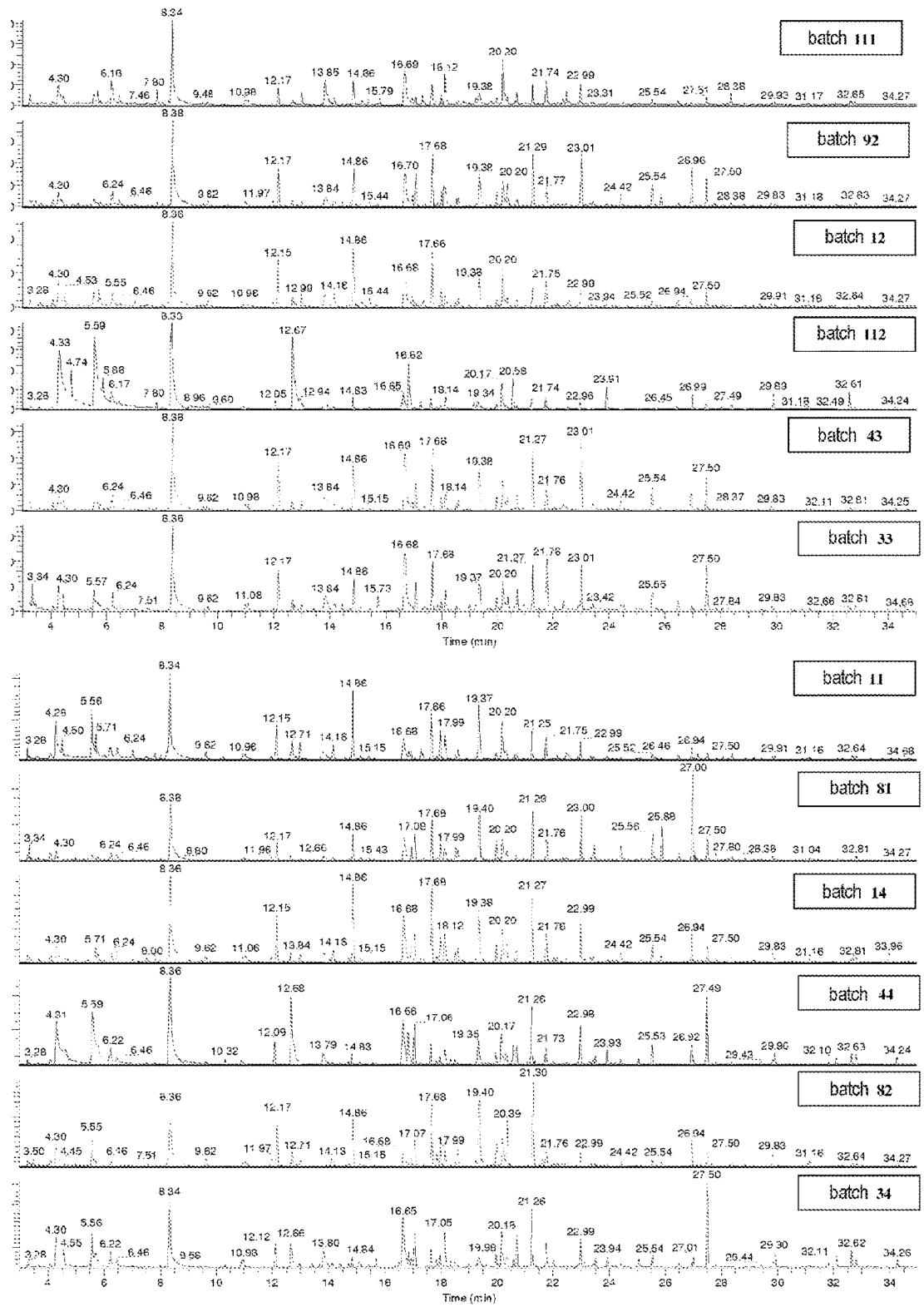
FIG. 2: Chromatograms (TIC) of the volatile organic compounds taken from samples by SPME in aqueous suspension
Figure 2:
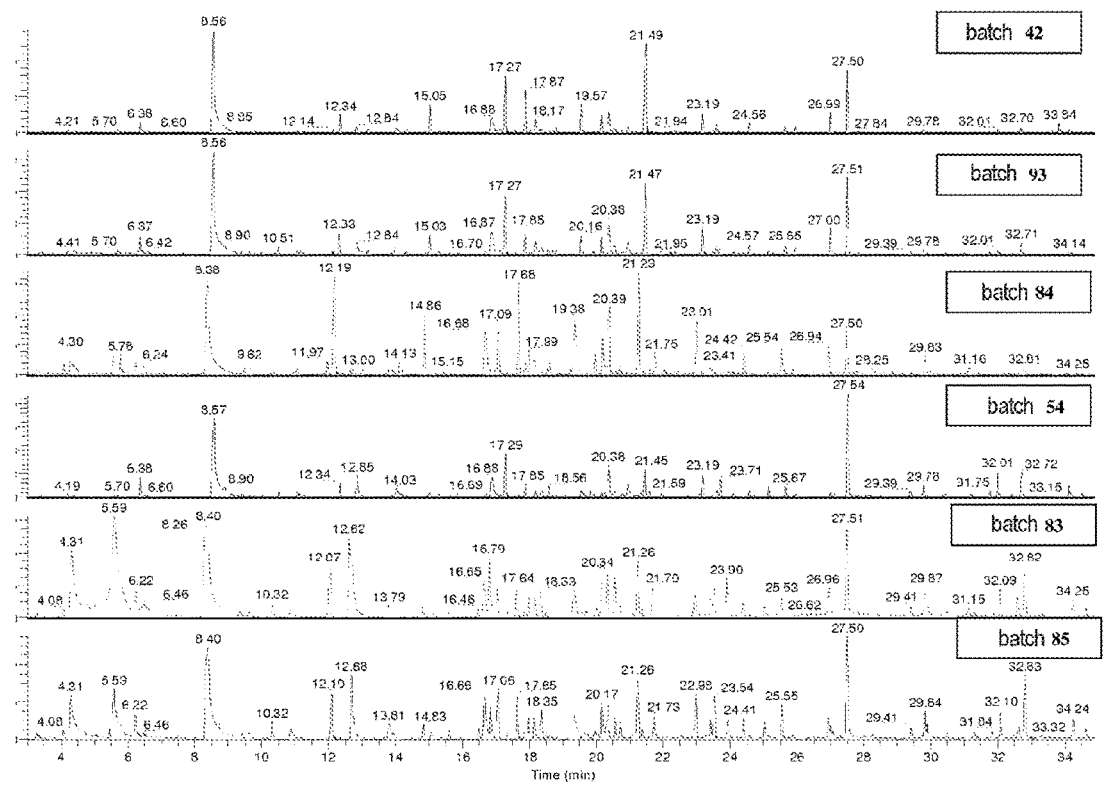
Figure 3:
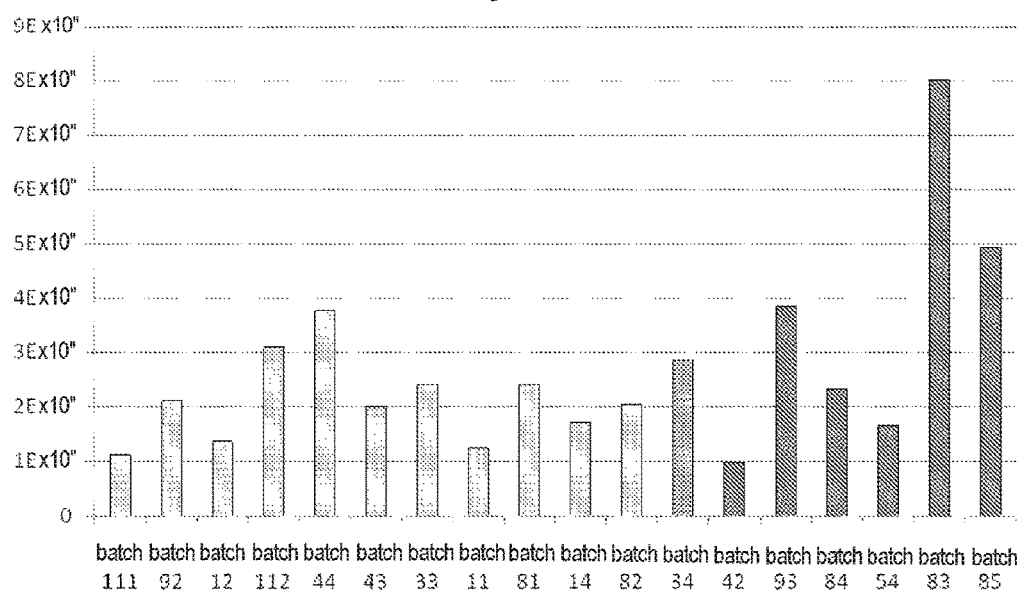
FIG. 3: Integration of all the peaks for the zone 3.2-35.0 min of the chromatograms (SPME in aqueous suspension)
Figure 4:
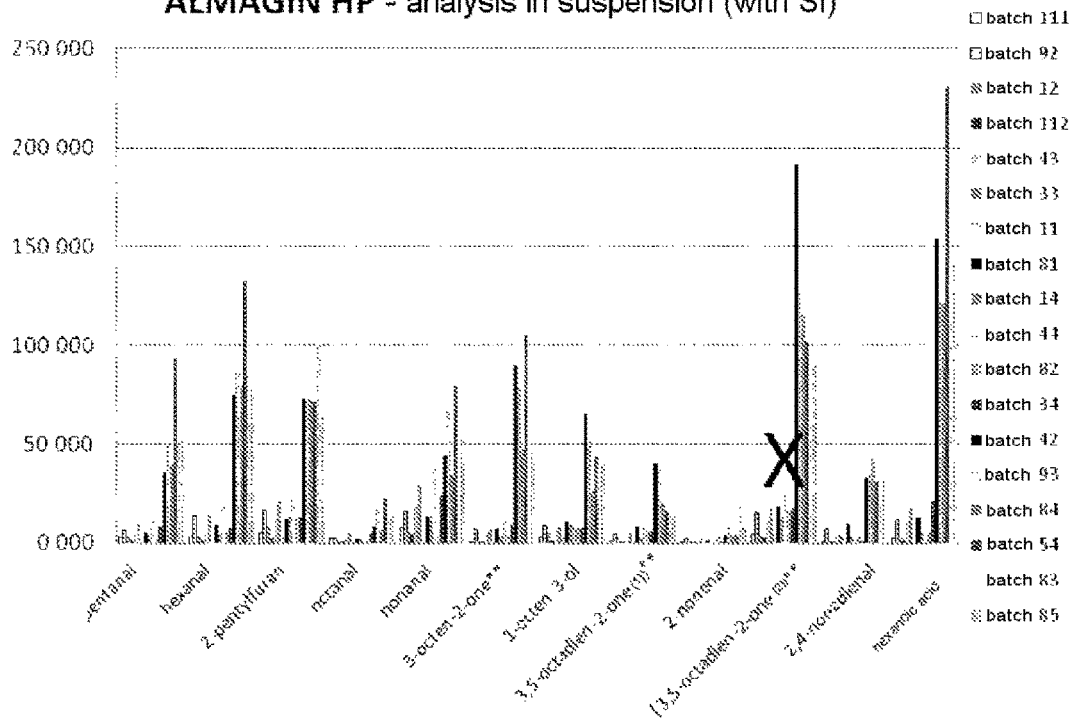
FIG. 4: Relative contents of 11 selected compounds taken from the sample space by SPME in aqueous suspension
Figure 5:
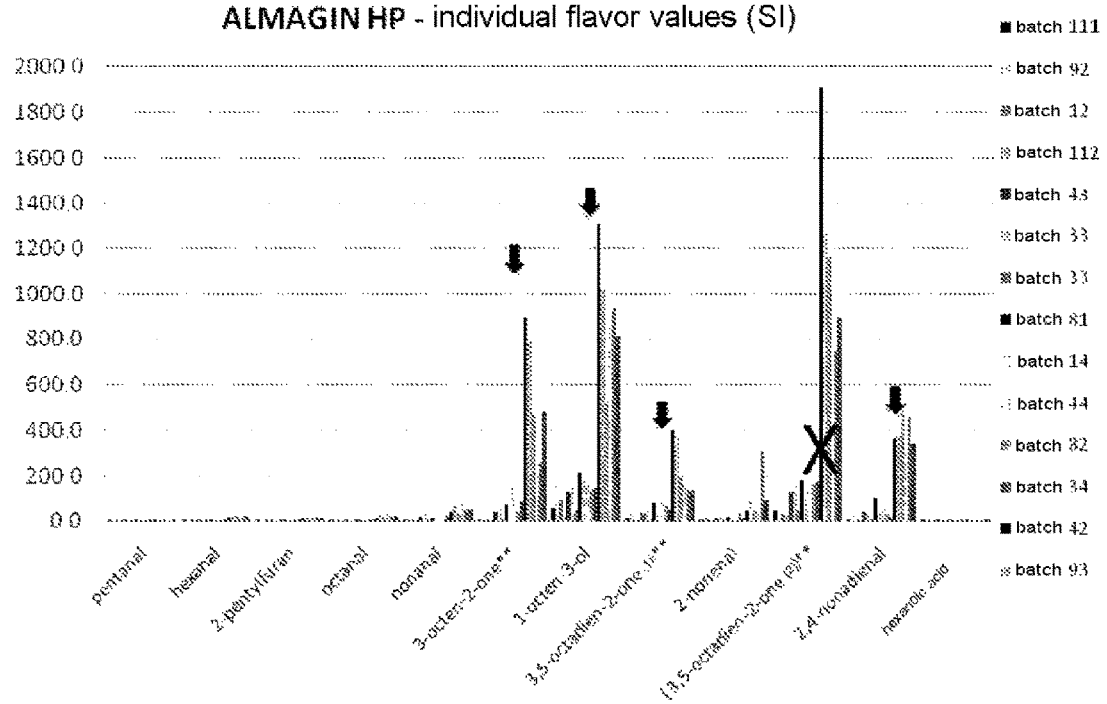
FIG. 5: Individual flavor values for the 11 compounds selected
Figure 6:
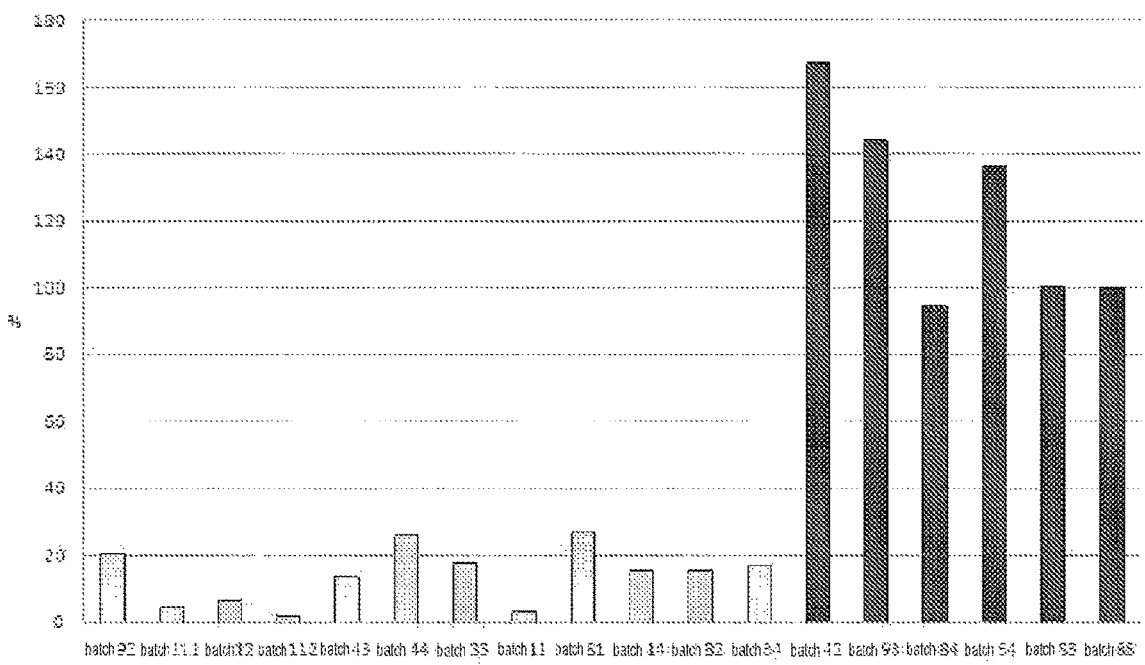
FIG. 6: Overall flavor value based on 4 compounds

The invention claimed is:

1. A method for determining the organoleptic quality of a protein-rich microalgal biomass composition, comprising determining the content of 11 volatile organic compounds, the 11 volatile organic compounds being pentanal, hexanal, 1-octen-3-ol, 2-pentylfuran, octanal, 3,5-octadien-2-ol (or 3-octen-2-one), 3,5-octadien-2-one, nonanal, 2-nonenal, (E,E)-2,4-nonadienal and hexanoic acid, characterized in that the microalgal biomass comprises more than 50% proteins by dry weight of biomass and in that the microalgae are of the *Chlorella* genus.

2. The method as claimed in claim 1, wherein the content of 11 volatile organic compounds is determined by SPME/GC of by SPME/GC-MS.

3. The method as claimed in claim 2, characterized in that the content of 11 volatile organic compounds is determined by the surface area of the chromatography peaks after SPME/GC.

4. The method as claimed in claim 1, characterized in that the content of 11 volatile organic compounds is compared to that of a reference protein-rich microalgal biomass or biomasses for which the organoleptic qualities are defined.

5. The method as claimed in claim 4, wherein the content of the 11 volatile organic compounds is determined by the surface area of the chromatography peaks corresponding to the 11 volatile organic compounds and compared to the content of the 11 volatile organic compounds in the reference protein-rich microalgal biomass or biomasses for which the organoleptic qualities are defined.

6. The method as claimed in claim 1, characterized in that the microalgae are selected from the group consisting of *Chlorella vulgaris*, *Chlorella sorokiniana* and *Chlorella protothecoides*.

7. The method as claimed in claim 6, wherein the microalgae is *Chlorella protothecoides*.

8. A method for defining an analytical profile of volatile organic compounds making it possible to evaluate the organoleptic quality of the protein-rich microalgal biomass compositions, comprising:
 the construction of a first matrix associating microalgal biomass compositions, including two controls of acceptable and unacceptable organoleptic quality, with the evaluation of their organoleptic qualities by a sensory panel of at least 15 individuals,
 the construction of a second matrix associating with these same compositions their characterization by a volatile organic compound analysis profile, and
 the correlation of the first matrix with the second to produce a relationship model on the basis of which the compositions having an optimized organoleptic profile can thus be characterized by their analytical profile of volatile organic compounds;
 characterized in that the microalgal biomass comprises more than 50% proteins by dry weight of biomass and in that the microalgae are of the *Chlorella* genus.

9. The method as claimed in claim 8, characterized in that the descriptors of the sensory analysis comprise:
 the following odors: vegetable, mash, stock, rancid butter, cheese, manure, fermented, peanut and paint; and
 the following colors: yellow and green.

10. A method for determining the organoleptic quality of a protein-rich microalgal biomass composition, comprising determining the content of 4 volatile organic compounds, these 4 organic compounds being 3,5-octadien-2-ol (or 3-octen-2-one), 1-octen-3-ol, 3,5-octadien-2-one and (E,E)-2,4-nonadienal and calculating an overall flavor value from the sum of the individual flavor values of 3,5-octadien-2-ol (or 3-octen-2-one), 1-octen-3-ol, 3,5-octadien-2-one and (E,E)-2,4-nonadienal,
 characterized in that the microalgal biomass comprises more than 50% proteins by dry weight of biomass and in that the microalgae are of the *Chlorella* genus.

11. The method as claimed in claim 10, characterized in that the microalgae are selected from the group consisting of *Chlorella vulgaris*, *Chlorella sorokiniana* and *Chlorella protothecoides*.

12. The method as claimed in claim 11, wherein the microalgae is *Chlorella protothecoides*.

13. A method for selecting protein-rich microalgal biomass compositions having an acceptable organoleptic profile, characterized in that the organoleptic quality is determined by the method as claimed in 9, and that the composition is selected when the overall flavor value calculated by the method is between 0 and 40% relative to that of an organoleptically unacceptable reference microalgal biomass composition, characterized in that the microalgal biomass comprises more than 50% proteins by dry weight of biomass and in that the microalgae are of the *Chlorella* genus.

* * * * *